(12) United States Patent
Wainless et al.

(10) Patent No.: US 11,103,058 B2
(45) Date of Patent: Aug. 31, 2021

(54) ORAL CARE IMPLEMENT

(71) Applicant: Colgate-Palmolive Company, New York, NY (US)

(72) Inventors: Daniel Wainless, New Brunswick, NJ (US); Patrik Johansson, Hoboken, NJ (US); Soniya Khan, Sayreville, NJ (US)

(73) Assignee: Colgate-Palmolive Company, New York, NY (US)

( * ) Notice: Subject to any disclaimer, the term of this patent is extended or adjusted under 35 U.S.C. 154(b) by 216 days.

(21) Appl. No.: 15/634,964

(22) Filed: Jun. 27, 2017

(65) Prior Publication Data

US 2018/0368566 A1    Dec. 27, 2018

(51) Int. Cl.
| A46B 15/00 | (2006.01) |
| A46B 9/04 | (2006.01) |
| A46B 9/00 | (2006.01) |
| A46B 11/00 | (2006.01) |
| A61Q 11/00 | (2006.01) |
| A61K 8/72 | (2006.01) |

(52) U.S. Cl.
CPC .......... *A46B 15/0022* (2013.01); *A46B 9/005* (2013.01); *A46B 9/04* (2013.01); *A46B 11/002* (2013.01); *A46B 11/0003* (2013.01); *A46B 11/0068* (2013.01); *A46B 15/0081* (2013.01); *A61K 8/72* (2013.01); *A61Q 11/00* (2013.01); *A46B 2200/1066* (2013.01); *A61K 2800/83* (2013.01); *A61K 2800/87* (2013.01)

(58) Field of Classification Search
CPC ...... A61N 1/0436; A61N 1/0548; A46B 9/04; A46B 15/0024; A46B 9/005; A46B 15/0081; A46B 11/0003; A46B 11/002; A46B 11/0068; A61K 8/72; A61Q 11/00
See application file for complete search history.

(56) References Cited

U.S. PATENT DOCUMENTS

| 3,520,297 | A | 7/1970 | Bechtold |
| 7,975,341 | B2 | 7/2011 | Cai et al. |
| 8,156,602 | B2 | 4/2012 | Jimenez et al. |
| 8,734,421 | B2 | 5/2014 | Sun et al. |
| 9,597,496 | B1 | 3/2017 | Johansson et al. |
| 2006/0010628 | A1* | 1/2006 | Moskovich ........ A46B 15/0055 15/111 |

(Continued)

FOREIGN PATENT DOCUMENTS

WO    WO01/30198    5/2001

*Primary Examiner* — Orlando E Aviles
*Assistant Examiner* — Joel D Crandall

(57) ABSTRACT

An oral care implement having electrodes thereon. In one aspect, the oral care implement may include a handle and a head, the head having a front surface and an opposite rear surface. A plurality of tooth cleaning elements may extend from the front surface of the head. A soft tissue cleaner may be located on the rear surface of the head, the soft tissue cleaner including a protuberance field. A first electrode and a second electrode are each operably coupled to a power source to have opposite electrical charges. The first and second electrodes may be spaced apart from one another and substantially surround the protuberance field. In other embodiments, the first and second electrodes may be embedded within or otherwise located within the protuberance field.

19 Claims, 24 Drawing Sheets

(56) References Cited

U.S. PATENT DOCUMENTS

| | | | |
|---|---|---|---|
| 2006/0070195 A1* | 4/2006 | Morita | A46B 15/0016 15/105 |
| 2007/0212665 A1* | 9/2007 | Jimenez | A61C 17/16 433/215 |
| 2007/0232983 A1* | 10/2007 | Smith | A61N 1/0444 604/20 |
| 2011/0289699 A1* | 12/2011 | Schaefer | A46B 15/0002 15/4 |
| 2015/0230593 A1* | 8/2015 | Doll | A46B 15/0006 702/19 |
| 2016/0184065 A1 | 6/2016 | Johansson et al. | |
| 2016/0338814 A1* | 11/2016 | Cho | A61C 19/06 |
| 2017/0209692 A1* | 7/2017 | Levi | A61N 1/26 |

* cited by examiner

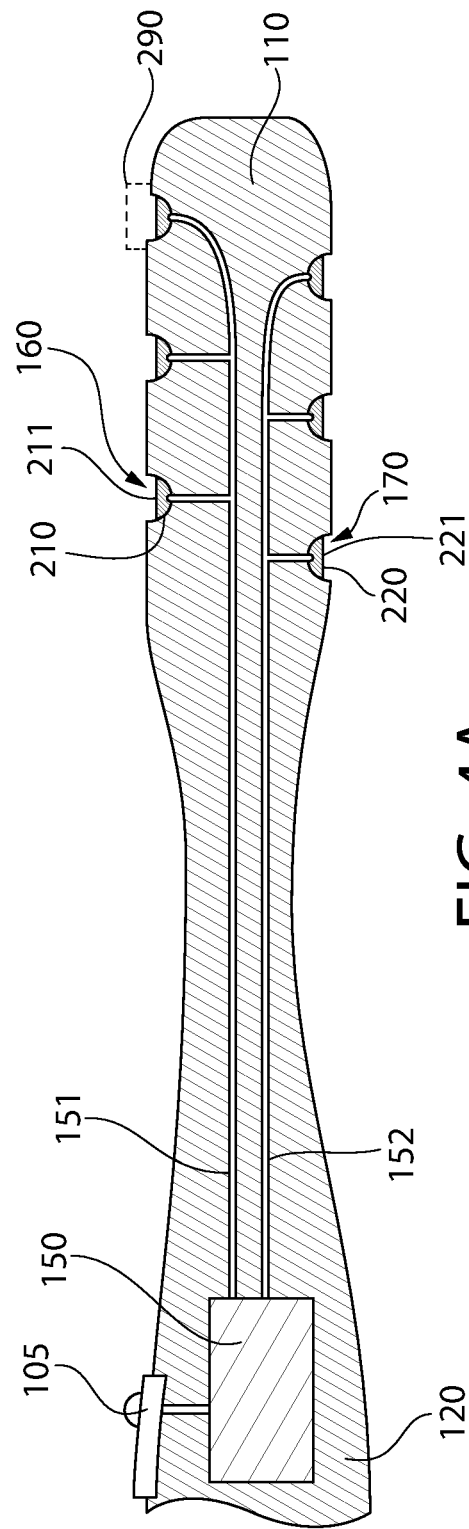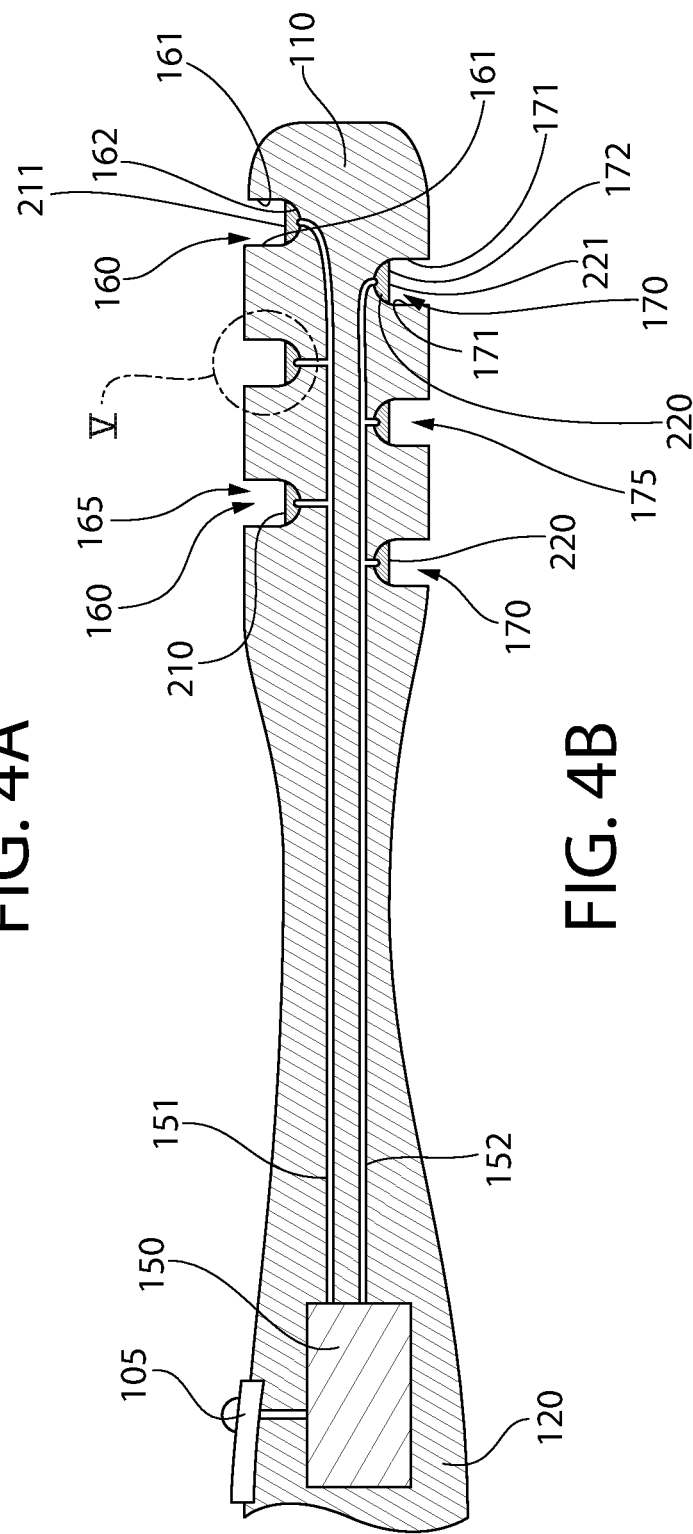
FIG. 4A
FIG. 4B

ORAL CARE IMPLEMENT

BACKGROUND

Toothbrushes are used to clean a person's oral cavity including the teeth and gums. Typically, dentifrice is placed on the bristles of the toothbrush to act as a cleaning agent. However, dentifrice is not always available and when it is available it is not always sufficient for cleaning. Recent developments in toothbrush and dentifrice manufacture have attempted to find better mechanisms to enhance the cleaning result during toothbrushing. Thus, there is a continuing need to develop oral care implements such as toothbrushes that have an increased cleaning potential in a wide range of environments.

BRIEF SUMMARY

The present invention is directed to an oral care implement having electrodes thereon. In one aspect, at least one of the electrodes may be a sacrificial electrode. The electrodes may be recessed relative to an exposed surface of the oral care implement body. The electrodes may be positioned around or within a soft tissue cleaner. The oral care implement may include a head having a through-hole, and the electrodes may be positioned on an upper and/or lower surface of the through-hole. The oral care implement may also include an oral care agent dispenser such that the electrodes are positioned near or adjacent to the oral care agent dispenser. The oral care agent dispenser may be a solid release polymer or an outlet that is coupled to a reservoir containing an oral care agent.

In one aspect, the invention may be an oral care implement comprising: a handle; a head coupled to the handle, the head having an exposed outer surface; a first depression formed in the exposed outer surface of the head; a first sacrificial electrode disposed within the first depression and having an exposed surface that is recessed relative to the exposed outer surface of the head; a second electrode on the head; and each of the first and second electrodes operably coupled to a power source to have opposite electrical charges.

In another aspect, the invention may be an oral care implement comprising: a handle; a head coupled to the handle, the head having a front surface and a rear surface opposite the front surface; a plurality of tooth cleaning elements extending from the front surface of the head; a soft tissue cleaner on the rear surface of the head, the soft tissue cleaner comprising a protuberance field; and a first electrode and a second electrode each operably coupled to a power source, the first and second electrodes spaced apart from one another and substantially surrounding the protuberance field.

In yet aspect, the invention may be an oral care implement comprising: a handle; a head coupled to the handle, the head having a front surface and a rear surface opposite the front surface; a plurality of tooth cleaning elements extending from the front surface of the head; a soft tissue cleaner positioned on the rear surface of the head, the soft tissue cleaner comprising a protuberance field; a first electrode and a second electrode each operably coupled to a power source and located at least partially within the protuberance field of the soft tissue cleaner; and wherein at least one of the first and second electrodes is a sacrificial electrode.

In still another embodiment, the invention may be an oral care implement comprising: a handle; a head coupled to the handle, the head having a front surface and a rear surface opposite the front surface; a plurality of tooth cleaning elements extending from the front surface of the head; a soft tissue cleaner formed of an elastomeric material positioned on the rear surface of the head; and a first electrode and a second electrode each operably coupled to a power source, at least one of the first and second electrodes embedded within the elastomeric material of the soft tissue cleaner.

In a further embodiment, the invention may be an oral care implement comprising: a handle; a head coupled to the handle and extending from a proximal end to a distal end along a longitudinal axis, the head comprising a front surface, a rear surface opposite the front surface, and a side surface extending between the front and rear surfaces; a transverse through-hole extending from a first opening in the side surface of the head to a second opening in the side surface of the head, the transverse through-hole forming a passageway through the head that is bounded by an upper surface and a lower surface; a first electrode and a second electrode operably coupled to a power source and located on the head; and wherein the first electrode is located on one of the upper and lower surfaces of the passageway so that an exposed outer surface of the first electrode faces the passageway.

In a still further embodiment, the invention may be an oral care implement comprising: a handle; a head coupled to the handle and comprising a front surface, a rear surface opposite the front surface, and first and second lateral surfaces extending between the front and rear surfaces; a plurality of tooth cleaning elements extending from the front surface of the head; a through-hole formed through the head from the first lateral surface of the head to the second lateral surface of the head, the through-hole being defined by an upper surface and a lower surface; a first electrode operably coupled to a power source and located on the upper surface of the through-hole; and a second electrode operably coupled to the power source and located on the lower surface of the through-hole.

In yet another embodiment, the invention may be an oral care implement comprising: a handle; a head coupled to the handle and comprising an outer surface; a plurality of tooth cleaning elements extending from the outer surface of the head; at least one oral care agent dispenser located on the outer surface of the head; a first electrode and a second electrode operably coupled to a power source to have opposite electrical charges, the first and second electrodes positioned on the outer surface of the head adjacent to the oral care agent dispenser; and wherein at least one of the first and second electrodes is a sacrificial electrode.

In still another embodiment, the invention may be an oral care implement comprising: a handle; a head coupled to the handle and having a first surface and an opposite second surface; a plurality of tooth cleaning elements extending from the first surface of the head; at least one oral care agent dispenser located on the second surface of the head; a first electrode and a second electrode operably coupled to a power source to have opposite electrical charges, the first and second electrodes positioned on the second surface of the head; and wherein at least one of the first and second electrodes is a sacrificial electrode.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4A is a cross-sectional view taken along line IVA-IVA of FIG. 2;

FIG. 4B is a cross-sectional view taken along line IVA-IVA of FIG. 2 in accordance with an alternative embodiment;

DETAILED DESCRIPTION

Figure 1:
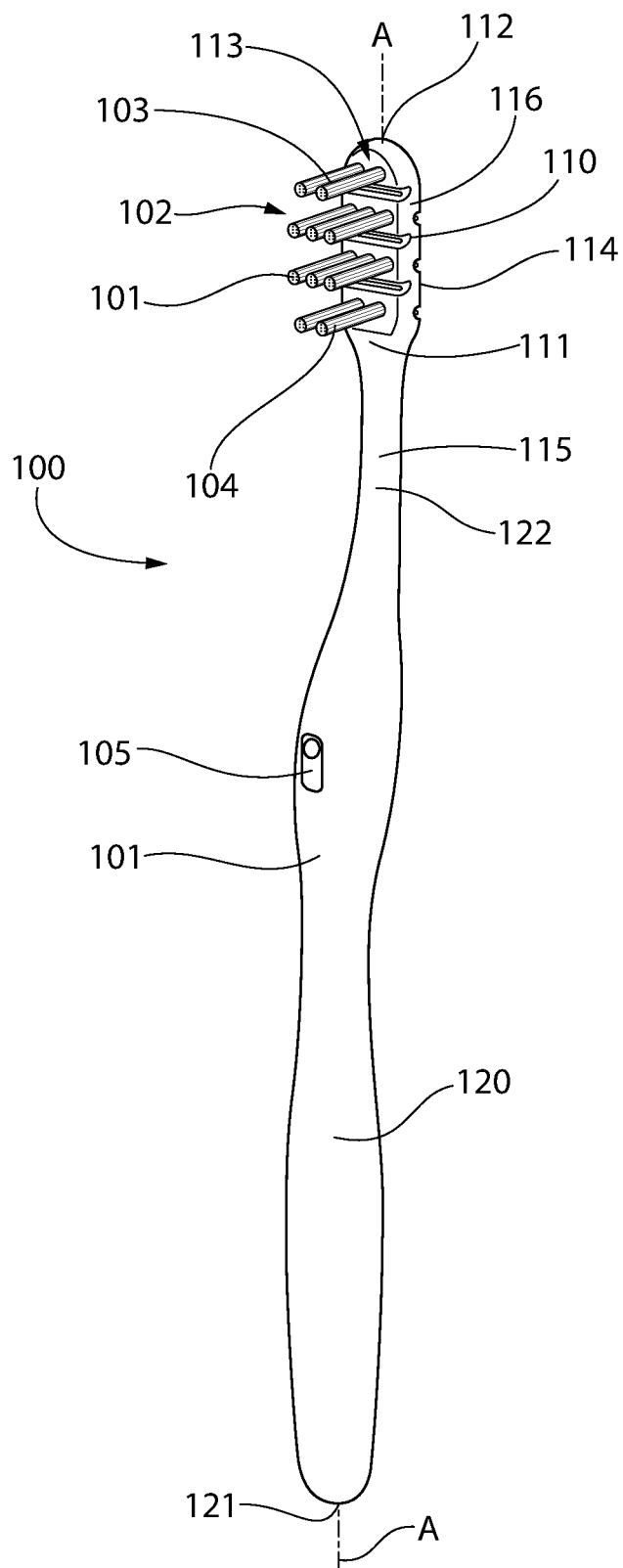
FIG. 1 is front perspective view of an oral care implement in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Referring first to FIG. 1, an oral care implement 100 is illustrated in accordance with an embodiment of the present invention. In the exemplified embodiment, the oral care implement 100 is in the form of a manual toothbrush. However, in certain other embodiments the oral care implement 100 can take on other forms such as being a powered toothbrush (having a vibrating or otherwise moving head/cleaning element section), a tongue scraper, a gum and soft tissue cleanser, a water pick, an interdental device, a tooth polisher, a specially designed ansate implement having tooth engaging elements or any other type of implement that is commonly used for oral care. Furthermore, although described herein as being an oral care implement, the inventive device may also be a personal care implement such that it is an implement used for personal care but not necessarily for oral care, such as a razor, a hairbrush, a makeup applicator, or the like. Thus, it is to be understood that the inventive concepts discussed herein can be applied to any type of oral care implement or personal care implement unless a specific type of oral care implement or personal care implement is specified in the claims.

The oral care implement 100 generally includes an elongated body 101 comprising a head 110, a neck 115 and a handle 120. The handle 120 extends from a distal end 121 to a proximal end 122 and the head 110 extends from a proximal end 111 to a distal end 112. The neck 115 extends between the proximal end 122 of the handle 120 and the proximal end 111 of the head 110. The oral care implement 100 extends along a longitudinal axis A-A from the distal end 121 of the handle 120 to the distal end 112 of the head 110. The head 110 also extends along the longitudinal axis A-A from the proximal end 111 to the distal end 112.

The handle 120 is an elongated structure that provides the mechanism by which the user can hold and manipulate the oral care implement 100 during use. In the exemplified embodiment, the handle 120 is generically depicted having various contours for user comfort. More specifically, in the exemplified embodiment the handle 120 is bulbous shaped and has a larger diameter in a central region than near the distal end 121 and the neck 115. Specifically, a region of the handle 120 that would normally be gripped by a user's thumb has a width that is greater than a width of the neck 115. Of course, the invention is not to be so limited in all embodiments and in certain other embodiments the handle 120 can take on a wide variety of shapes, contours and configurations, none of which are limiting of the present invention unless so specified in the claims.

In the exemplified embodiment, the handle 120 is formed of a rigid plastic material, such as for example without limitation polymers and copolymers of ethylene, propylene, butadiene, vinyl compounds and polyesters such as polyethylene terephthalate. Of course, the invention is not to be so limited in all embodiments and the handle 120 may include a resilient material, such as a thermoplastic elastomer, as a grip cover that is molded over portions of or the entirety of the handle 120 to enhance the gripability of the handle 120 during use. For example, portions of the handle 120 that are typically gripped by a user's palm during use may be overmolded with a thermoplastic elastomer or other resilient material to further increase comfort to a user.

The head 110 of the oral care implement 100 is coupled to the handle 120 and comprises an exposed outer surface that includes a front surface 113, an opposing rear surface 114, and a side surface 116 extending between the front and rear surfaces 113, 114. The exposed outer surface of the head 110 is any portion of the head 110 that is directly exposed to the ambient environment and is visible to a viewer. In the exemplified embodiment, the head 110 is formed integrally with the handle 120 as a single unitary structure using a molding, milling, machining or other suitable process. However, in other embodiments the handle 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

In the exemplified embodiment, the head 110 of the oral care implement 100 is provided with a plurality of tooth cleaning elements 101 extending from the front surface 113. The tooth cleaning elements 101 collectively form a tooth cleaning element field 102 that comprises a distal-most cleaning element 103 located adjacent the distal end 112 of the head 110 and a proximal-most cleaning element 104 located adjacent the proximal end 111 of the head 110.

Although in the exemplified embodiment all of the tooth cleaning elements 101 appear to be the same in terms of material, structure, shape, and length, the invention is not to be so limited in all embodiments. Thus, the exact structure, pattern, orientation and material of the tooth cleaning elements 101 is not to be limiting of the present invention unless so specified in the claims. Thus, as used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, multi-component bristles including spiral bristles and core-sheath bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 101 of the present invention can be connected to the head 110 in any manner known in the art. For example, staples/anchors, in-mold tufting (IMT) or anchor free tufting (AFT) could be used to mount the cleaning elements/tooth engaging elements. In certain embodiments, the invention can be practiced with various combinations of stapled, IMT or AFT bristles. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In the exemplified embodiment, the head 110 of the oral care implement 100 comprises a plurality of tuft holes 102 (FIG. 2) formed therein. A plurality of tufts of bristles are positioned within and affixed to the head 110 within each of the tuft holes. Each of the tufts of bristles includes a plurality of bristles, which can be single strand bristles, double strand multi-component bristles, triple strand multi-component bristles, etc. or various combinations thereof. Additionally, a single tuft hole may be filled with an elastomeric cleaning element or any of the other types of cleaning elements noted above.

Although not illustrated herein in this embodiment (shown and described in more detail below with reference to FIGS. 12, 13, 15, 16A, 16B), in certain embodiments the head 110 may also include a soft tissue cleanser coupled to or positioned on its rear surface 113. An example of a suitable soft tissue cleanser that may be used with the present invention and positioned on the rear surface 114 of the head 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

Figure 2:
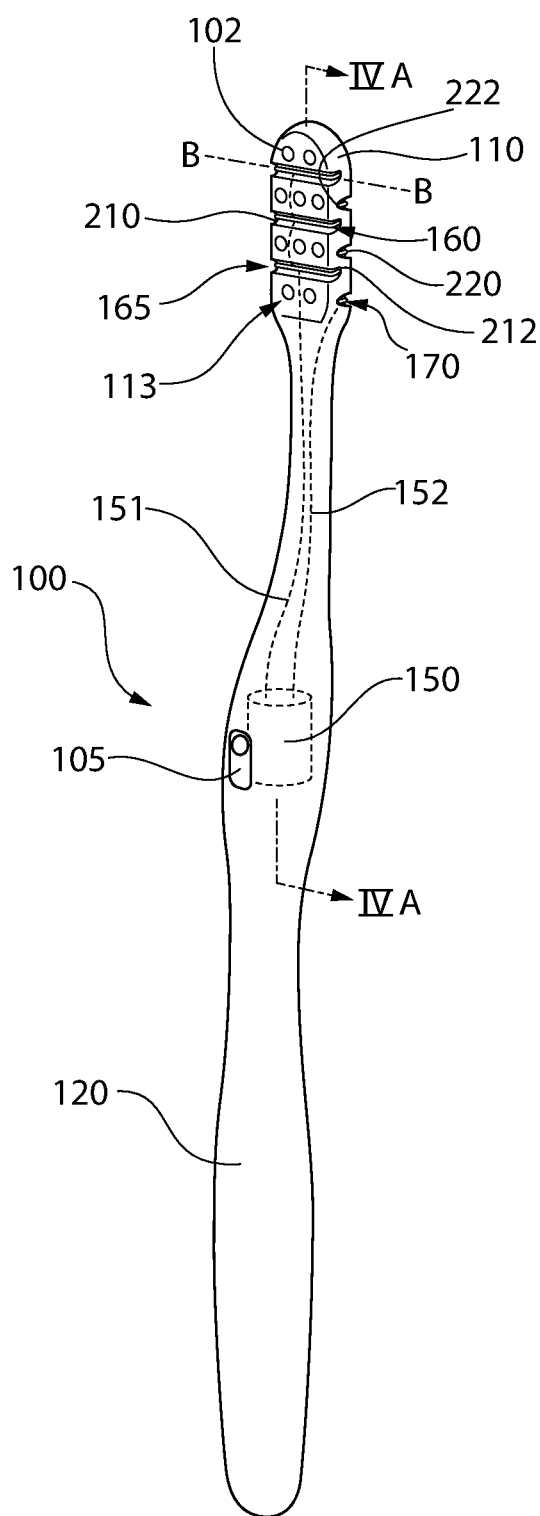
FIG. 2 is a front perspective view of the oral care implement of FIG. 1 with tooth cleaning elements removed and illustrating electrical components and connections using dashed lines.
Figure 3:
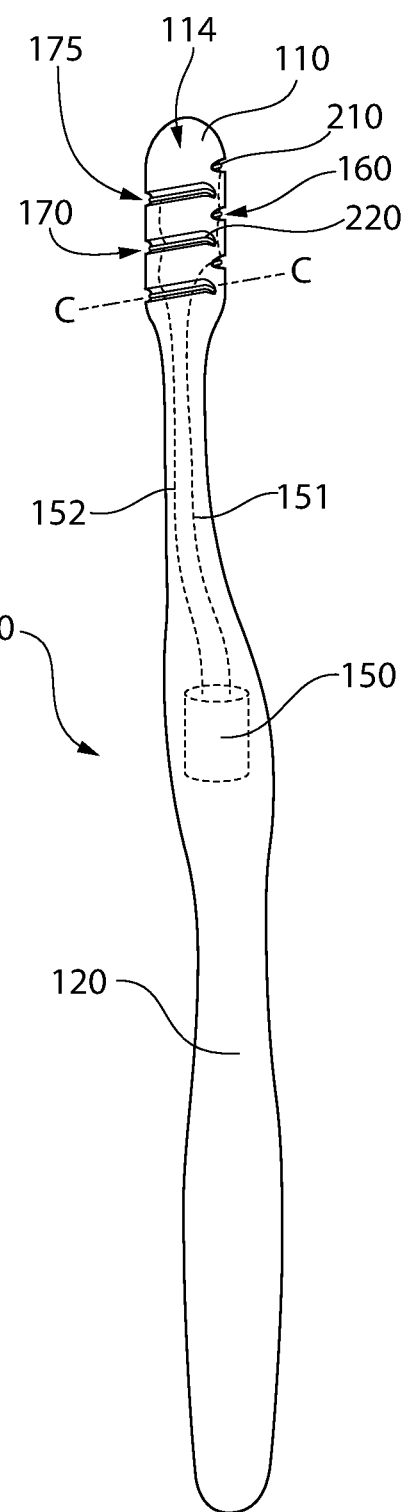
FIG. 3 is a rear perspective view of the oral care implement of FIG. 2.

Referring to FIGS. 1-3 concurrently, the oral care implement 100 includes a power source 150, a first electrode 210 and a second electrode 220. In the exemplified embodiment, the power source 150 is located within the handle 120 of the oral care implement 100, but the power source 150 may be located in the neck 115 or the head 110 in other embodiments or power may be provided to the electrodes via an external power source. In the exemplified embodiment, the power source 150 is a battery. However, any power source may be used including solar power or the like. In fact, in some embodiments the oral care implement 100 may include a power cord so that the oral care implement 100 may be coupled directly to a wall socket as the power source. In other embodiments, the power source may be residual power that is configured to provide a charge to the first and second electrodes 210, 220 during use of the oral care implement 100. The power source 150 is coupled to the first and second electrodes 210, 220 that are located on the oral care implement 100 as will be described in greater detail below.

A closed circuit is formed between the power source 150 and the first and second electrodes 210, 220 when an electrolyte (e.g., a user's saliva or a toothpaste slurry) extends between a pair of the first and second electrodes 210, 220, which have opposite charges as described herein below. Thus, when the power source 150 is activated, an electrical field is created between the pair of the first and second electrodes 210, 220. More specifically, the electrodes 210, 220 may be positioned to act as an anode and a cathode (i.e., by having opposite charges). One of the electrodes 210, 220 may always be an anode while the other electrode 120, 220 is always a cathode, or they may switch during operation. The toothbrush may also include a controller and/or additional electronics. For example, the controller may control current and/or voltage from the power source 150 to the electrodes 210, 220. In some embodiments, the controller may alternate the current through the electrodes 210, 220 and/or otherwise control the current, such as through pulse width modulation or alternating the current through the coils, to achieve desired activation sequences of the electrodes 210, 220. The controller may also include a timing mechanism, such that the electrodes 210, 220 are activated for a predetermined time, for example.

In one embodiment, at least one of the first and second electrodes 210, 220 is a sacrificial electrode (made of a sacrificial metal such as zinc, copper, silver, or the like) and passing a current from the power source 150 to the first and second electrodes 210, 220 causes the sacrificial electrode(s) to oxidize and release ions. This process and its benefits will be described more thoroughly below. Thus, providing electrical current to the electrode system may be useful to provide oral health benefits in addition to the benefits obtained by use of the tooth cleaning elements 101. The electrode system may be controlled, at least in part, by a user operating the oral care implement 100 via an actuator component.

Specifically, in the exemplified embodiment the oral care implement 100 comprises an actuator component 105 positioned on the handle 120 and operably coupled to the power source 150 or to the conductors that couple the electrodes 210, 220 to the power source 150. The actuator component 105 may be a switch (such as a button switch, a slide switch, a toggle switch, a conductive capacitor-type switch or the like) that dictates whether or not current is supplied from the power source 150 to the electrodes 210, 220 of the oral care implement 100. Thus, if the actuator component 105 is in a first position, a circuit is closed and current is supplied from the power source 150 to the electrical components of the oral care implement 100 whereas if the actuator component 150 is in a second position, the circuit is open and power is not able to be supplied from the power source 150 to the electrical components of the oral care implement 100. In other embodiments, the actuator component 105 may be omitted and an electric field may be generated between the first and second electrodes 210, 220 when an electrolyte (i.e., saliva) spans between one of the first and second electrodes 210, 220.

In certain embodiments, at least one of the first and second electrodes 210, 220 may be a sacrificial electrode. Specifically, in some embodiments the first electrode 210 may be a sacrificial electrode while the second electrode 220 is not. In other embodiments the second electrode 220 may be a sacrificial electrode while the first electrode 210 is not. In still other embodiments, both of the first and second electrodes 210, 220 (or all of the first electrodes 210 and all of the second electrodes 220 when there is more than one of each as discussed in greater detail below) may be sacrificial electrodes. A sacrificial electrode includes a sacrificial metal, and when current is applied to the first and second electrodes 210, 220, the sacrificial electrode gives up ions by oxidizing. In one presently preferred embodiment, the sacrificial electrode includes zinc and the presence of an electrical potential oxidizes the zinc to release $Zn^{2+}$. Zinc ions are conventionally known to provide oral health benefits including for example anti-bacterial benefits. In this example, the zinc ions are released from at least one of the first and second electrodes 210, 220 (whichever is a sacrificial electrode) and into the user's oral cavity to provide the user with anti-bacterial benefits. In some embodiments the sacrificial electrode may be formed entirely from the sacrificial metal, whereas in other embodiments the sacrificial electrode may be plated with the sacrificial metal.

As mentioned above, the sacrificial metal may be zinc, but the invention is not to be so limited in all embodiments. In other implementations, for example, the sacrificial electrode may include different metals that can be oxidized to provide ions that give alternative oral benefits. For example, tin ions, i.e., $Sn2+$ and $Sn4+$ have known oral health benefits and the sacrificial electrode could include tin. Moreover, the oxidation of iron and/or manganese can drive the formation of hydroxide radicals from hydrogen peroxide, e.g., via the fenton reaction, which may provide other benefits in the oral cavity. Furthermore, different sacrificial metals may be used on different ones of the sacrificial electrodes. Thus, combinations of electrodes including zinc, tin, iron, manganese, or the like may be used on the oral care implement 100.

The exemplary embodiments shown in the drawings and described herein illustrate example devices related to oral health that incorporate electrodes. In certain embodiments, at least one of the electrodes is a sacrificial electrode, made of a sacrificial metal. For example, the sacrificial electrode may be made of zinc, which may be 90% or more pure zinc. When an electrical potential is produced across the electrodes, zinc ions are released into an electrolyte, which may be saliva, water, or a dentifrice. In embodiments of this disclosure, the electrolyte is then transferred to the oral cavity to provide a benefit to the oral cavity. For example, when zinc is used as the sacrificial metal, the electrolytic fluid will carry zinc ions, which act as an antibacterial agent in the oral cavity. Other sacrificial metals, such as iron, or tin, may also or alternatively be used, to provide other or additional oral benefits. When the electrolyte used is a dentifrice solution, such as a mouthwash or tooth whitening agent, the electrodes may also act to activate components in the dentifrice. The zinc or other ions may enhance already existing products, including those whose original purpose may have been other than therapeutic. The oral care implement 100 may in some embodiments include sacrificial electrodes comprising zinc and sacrificial electrodes including one or more of tin, iron, manganese, or the like to provide a user with multiple benefits.

Controlling a current flowing between the first and second electrodes may be used to promote additional oral health benefits, to supplement the actions of the tooth cleaning elements. For example, the electrodes may interact with specific ingredients in a dentifrice slurry by converting relatively stable precursors in the dentifrice to active oxygen species and other therapeutic molecules. By way of non-limiting example, a slurry may be acted upon by the electrodes to generate oxidizing agents, such as $Cl_2$, $OCl^-$, and/or $HOCl$. In still other examples, the electrodes may be used to generate directly beneficial agents. For example, when one of the electrodes is made of zinc, selective energizing of the electrodes can generate different $Zn^{2+}$ species, which are effective anti-bacterial agents. In further examples still, the electrodes may be used to promote tooth-uptake of fluorine. The electrodes may also be used to suppress or mask breath or mouth malodor.

Referring to FIGS. 1-4A concurrently, in the exemplified embodiment the first and second electrodes 210, 220 are positioned on the head 110 of the oral care implement 100. During use of the oral care implement 100 to cleanse a user's teeth and other oral cavity surfaces, the head 110 is placed in the user's oral cavity and current is passed through the first and second electrodes 210, 220 to provide an electrochemical benefit in the oral cavity. As mentioned above, the benefit may include the release of ions or the like upon degradation of at least one of the first and second electrodes 210, 220 (when it is a sacrificial electrode). To promote the release of ions into the oral cavity, the first and second electrodes may be exposed to the environment of the oral cavity such that saliva and/or toothpaste slurry can act as an electrolytic solution.

In the exemplified embodiment, the oral care implement 100 includes three of the first electrodes 210 and three of the second electrodes 220, although more or less than three of each of the first and second electrodes 210, 220 may be used in other embodiments. Each of the first electrodes 210 is operably coupled to one of the positive and negative terminals of the power source 150 via a first electrical conductor (i.e., wire) 151 and each of the second electrodes 220 is operably coupled to the other of the positive and negative terminals of the power source 150 via a second electrical conductor (i.e., wire) 152. Thus, the first and second electrodes 210, 220 have an opposite electrical charge (the first electrodes 210 may have a positive charge (cathodes) while the second electrodes 220 have a negative charge (anodes) or the first electrodes 210 may have a negative charge while the second electrodes 220 have a positive charge).

In the exemplified embodiment, a first depression 160 and a second depression 170 are formed into the exposed outer surface of the head 110. More specifically, three of the first depressions 160 are formed into the front surface 113 of the head 110 and three of the second depressions 170 are formed into the rear surface 114 of the head 110. In the exemplified embodiment, each of the first electrodes 210 is positioned within one of the first depressions 160 and each of the second electrodes 220 is positioned within one of the second depressions 170. Of course, the first electrodes 210 need not be positioned solely on the front surface 113 of the head 110 and the second electrodes 220 need not be positioned solely on the rear surface 114 of the head 110 in all embodiments. Rather, in some embodiments there may be at least one of the first and second electrodes 210, 220 positioned on each of the front and rear surfaces 113, 114 of the head 110. Thus, one of the first electrodes 210 may be positioned within one of the second depressions 170 on the rear surface 114 of the head 110 and one of the second electrodes 220 may be positioned within one of the first depressions 160 on the front surface 113 of the head 110. Various combinations for the positioning of the first and second electrodes 210, 220 are possible within the scope of the disclosure set forth herein.

Due to the depth of the first and second depressions 160, 170 as discussed in more detail below with specific reference to FIG. 5, each of the first and second electrodes 210, 220 is recessed relative to the exposed outer surface of the head 110. Specifically, with reference to the exemplified embodiment, each of the first electrodes 210 is recessed relative to the front surface 113 of the head 110 and each of the second electrodes 220 is recessed relative to the rear surface 114 of the head 110. Thus, the first and second electrodes 210, 220 are sunken into the head 110 such that they are not flush with the exposed outer surface of the head 110 and they do not protrude from the exposed outer surface of the head 110.

Referring to FIG. 4A, each of the first electrodes 210 has an exposed surface 211. The exposed surfaces 211 of the first electrodes 210 are exposed to a viewer who is viewing the outer surface of the head 110, and more particularly the front surface 113 of the head 110. Furthermore, the exposed surfaces 211 of the first electrodes 210 are recessed relative to the front surface 113 of the head 110. Similarly, each of the second electrodes 220 has an exposed surface 221. The exposed surfaces 221 of the second electrodes 220 are exposed to a viewer who is viewing the outer surface of the head 110, and more particularly the rear surface 114 of the head 110. Furthermore, the exposed surfaces 221 of the second electrodes 220 are recessed relative to the rear surface 114 of the head 110.

Of course, at mentioned above the first electrodes 210 need not be on the front surface 113 of the head 110 in all embodiments and the second electrodes 220 need not be on the rear surface 114 of the head 110 in all embodiments. However, regardless of the exact location of the first and second electrodes 210, 220 on the head 110, the exposed surfaces 211, 221 of the first and second electrodes 210, 220 are recessed relative to the portion of the exposed outer surface of the head 110 that is adjacent to the respective one of the first and second electrodes 210, 220. Thus, the first and second electrodes 210, 220 are surrounded by a portion of the head 110 that protrudes beyond the exposed surfaces 211, 221 of the first and second electrodes 210, 220. By recessing the first and second electrodes 210, 220 within the head 110, the risk of a user feeling an electric shock during use of the oral care implement 100 is reduced if not eliminated.

Still referring to FIG. 4A, in the exemplified embodiment a cover member 290 is positioned over one of the first electrodes 210. The cover member 290 is illustrated generically using dotted lines, but it should be appreciated that the size, shape, and other structure of the cover member 290 is not to be limited based on that which is illustrated in the drawings. Specifically, the cover member 290 is any structure that can cover one or more of the first and second electrodes 210, 220 to further reduce the likelihood that a user's oral surfaces will come into direct contact with one of the first and second electrodes 210, 220.

In the exemplified embodiment, the cover member 290 is positioned over only one of the first electrodes 210. However, the invention is not to be so limited and in other embodiments each of the first and second electrodes 210, 220 may be covered by the cover member 290. Still further, various ones of the first and second electrodes 210, 220 may be covered by or not covered by the cover member 290. In some embodiments, the first and second electrodes 210, 220 need not be recessed relative to the outer surface of the head 110 because direct contact between a user's oral surfaces and the first and second electrodes 210, 220 may be prevented by the cover member 290. Thus, i some embodiments each of the electrodes 210, 220 that is recessed relative to the outer surface of the head 110 may be left uncovered whereas each of the electrodes 210, 220 that is flush with or protrudes from the outer surface of the head 110 may be covered by the cover member 290.

Such a cover member 290 may be formed of a mesh material or other material that is porous to liquid so that liquid such as saliva and toothpaste slurry can pass through the cover member 290 to act as an electrolyte and form an electric field between the first and second electrodes 210, 220 as described herein. The cover member 290 may be considered a permeable cover or screen in some embodiments because it is permeable to liquid. Thus, the cover member 290 prevents a user's oral cavity surfaces (tongue, gums, inner surfaces of the cheeks) from directly contacting the electrodes 210, 220 while permitting saliva and toothpaste slurry and other oral care agents as described herein to contact the electrodes 210, 220.

Referring to FIGS. 2, 3, 4B and 5 concurrently, the first and second depressions 160, 170 and the first and second electrodes 210, 220 will be described in greater detail. In the exemplified embodiment, each of the first depressions 160 is a first elongated groove 165 that extends along a first groove axis B-B. In the exemplified embodiment, the first depressions 160 extends across the entirety of the front surface 113 of the head 110 in a direction transverse to the longitudinal axis A-A. Furthermore, each of the first depressions 160 extends from a first open end located on the side surface 116 of the head 110 on a first side of the longitudinal axis A-A to a second open end located on the side surface 116 of the head 110 on an opposite side of the longitudinal axis A-A.

Each of the first depressions 160 is formed by opposing upstanding sidewalls 161 and a floor 162. In the exemplified embodiment the floor 162 has a contoured shape such that the first depressions 160 are U-shaped in cross-section. However, the invention is not to be so limited in all embodiments and the floor 162 of the first depression 160 may be linear and perpendicular to the upstanding sidewalls 161 in some embodiments so that the first depressions 160 are square or rectangular in cross-section. Alternatively, the sidewalls 161 may meet at an apex at the bottom of the first depression 160 such that the first depressions 160 have a V-shaped cross-sectional shape.

In the exemplified embodiment, one of the first electrodes 210 is positioned within each of the first depressions 160 so that the first electrode 210 covers the floor 162 of the first depression 160. In the exemplified embodiment, the first electrodes 210 have a shape that matches with the cross-sectional shape of a bottom portion of the first depression 160. However, the invention is not to be particularly limited by the shapes of the first electrodes 210 in all embodiments. The first elongated groove 165 of the first depression 160 is defined by the upstanding sidewalls 161 and the exposed surface 211 of the first electrode 210 that is positioned within the first depression 160. Thus, the floor of the first elongate groove 165 is formed by the exposed surface 211 of the first electrode 210. In the exemplified embodiment, an entirety of the floor of each of the first grooves 165 is formed by the exposed surface 211 of the one of the first electrodes 210 that is positioned within the respective first depression 160. However, in other embodiments the first electrodes 210 may only cover a portion of the floor 162 of the first depression 160.

Similarly, each of the second depressions 170 is a second elongated groove 165 that extends along a second groove axis C-C. In the exemplified embodiment, the second depressions 170 extend across the entirety of the rear surface 114 of the head 110 in a direction transverse to the longitudinal axis A-A. Furthermore, the second depressions 170 extend from a first open end located on the side surface 116 of the head 110 on a first side of the longitudinal axis A-A to a second open end located on the side surface 116 of the head 110 on an opposite side of the longitudinal axis A-A.

Each of the second depressions 170 is formed by opposing upstanding sidewalls 171 and a floor 172. The floor 172 is contoured similar to the floor 162, but need not be in all embodiments as described above. In the exemplified embodiment, the second electrodes 220 have a shape that matches with the cross-sectional shape of a bottom portion of the second depression 170. However, the invention is not to be particularly limited by the shapes of the second electrodes 220 in all embodiments. In the exemplified embodiment, one of the second electrodes 220 is positioned within each of the second depressions 170 so that the second electrode 220 covers the floor 172 of the second depression 160 within which it is positioned. The second elongated groove 175 of the second depression 170 is defined by the upstanding sidewalls 171 and the exposed surface 221 of the second electrode 220 that is positioned within the second depression 170. Thus, the floor of the second elongated groove 175 is formed by the exposed surface 221 of the second electrode 220. In the exemplified embodiment, an entirety of the floor 172 of each of the second grooves 175 is formed by the exposed surface 221 of the one of the second electrodes 220 that is positioned within the respective second depression 170. However, in other embodiments the second electrodes 220 may only cover a portion of the floor 172 of the second depression 170.

In the exemplified embodiment, each of the first depressions 160 is elongated in a direction of the first groove axis B-B and each of the second depressions 170 is elongated in a direction of the second groove axis C-C. Furthermore, the first and second depressions 160, 170 have a semi-cylindrical shape. Furthermore, in the exemplified embodiment the first and second electrodes 210, 220 have semi-circular cross-sectional shapes and may have semi-cylindrical shapes and be elongated in the direction of the first and second groove axes B-B, C-C, respectively. Thus, in the exemplified embodiment the first and second electrodes 210, 220 nest neatly within the first and second depressions 160, 170. However, the invention is not to be so limited and the shapes of the first and second depression 160, 170 and the first and second electrodes 210, 220 shown in the drawings are merely exemplary in nature and are not intended to be limiting of the present invention in all embodiments.

In the exemplified embodiment, the first and second depressions 160, 170 and the first and second electrodes 210, 220 are linear and they extend in a direction transverse to the longitudinal axis A-A. Thus, the first and second groove axes B-B, C-C are transverse or perpendicular to the longitudinal axis A-A. In other embodiments, the first and second depressions 160, 170 and the first and second electrodes 210, 220 may be non-linear such as being arcuate, contoured, wavy, or the like as they extend in a direction generally transverse to the longitudinal axis A-A. In still other embodiments, the first and second depressions 160, 170 may not extend in a direction transverse to the longitudinal axis A-A at all, but rather may extend so as to be oriented oblique or even parallel relative to the longitudinal axis A-A. In still other embodiments the first electrodes 210 may be annular or ring-shaped and the second electrodes 220 may be annular or ring-shaped. In some embodiments, the first and second electrodes 210, 220 may not be elongated at all, but rather may be circular or polygonal shaped and they may form a closed-geometry along the front and/or rear surfaces 113, 114 of the head 110 on which they are positioned.

In the exemplified embodiment, a single one of the first electrodes 210 is positioned within each of the first depressions 160 and a single one of the second electrodes 220 is positioned within each of the second depressions 170. However, the invention is not to be so limited and in some other embodiments there may be a plurality of the first electrodes 210 positioned in a spaced apart manner within each of the first depressions 160 and a plurality of the second electrodes 220 positioned in a spaced apart manner within each of the second depressions 170. Thus, there are many possible permutations regarding the size and shape of the first and second depressions 160, 170 and the first and second electrodes 210, 220. In some embodiments, it is merely necessary that the first and second electrodes 210, 220 are positioned in the first and second depressions 160, 170, respectively, in such a manner so that the exposed surfaces 211, 221 of the first and second electrodes 210, 220 are recessed relative to the exposed outer surface (i.e., the front surface 113, the rear surface 114, the side surface 116) of the head 110 on which that particular one of the first and/or second electrodes 210, 220 is located.

In the exemplified embodiment the first electrodes 210 are located on the front surface 113 of the head 110 and the second electrodes 220 are located on the rear surface 114 of the head 110. However, the invention is not to be so limited in all embodiments and in certain other embodiments at least one of the first electrodes 210 and at least one of the second electrodes 220 may be positioned on the front surface 113 and/or the rear surface 114 of the head 110. Thus, the front and/or rear surfaces 113, 114 of the head 110 may include at least one of each of the first and second electrodes 210, 220.

In the exemplified embodiment, only the first electrodes 210 are positioned on the front surface 113 of the head 110 and only the second electrodes 220 are positioned on the rear surface 114 of the head 110. The first electrodes 210 extend along the first groove axes B-B which are transverse to the longitudinal axis A-A and the second electrodes 220 extend along the second groove axes C-C which are transverse to the longitudinal axis A-A. More specifically, the first electrodes 210 are located on the head 110 in an axially spaced apart manner such that each of the first electrodes 210 on the front surface 113 of the head 110 is spaced apart from each of the other first electrodes 210 on the front surface 113 of the head 110. The second electrodes 220 are located on the head 110 in an axially spaced apart manner such that each of the second electrodes 220 on the rear surface 114 of the head 110 are spaced apart from each of the other second electrodes 220, on the rear surface 114 of the head 110.

In the exemplified embodiment, each of the first electrodes 210 on the front surface 113 of the head 110 is axially spaced apart from each of the second electrodes 220 on the rear surface 114 of the head 110. The first electrodes 210 and the second electrodes 220 are on opposite sides of the head 110 but are axially offset in their positioning on the head 110. Thus, a plane that is perpendicular to the front and rear surfaces 113, 114 of the head 110 that intersects one of the first electrodes 210 does not intersect any of the second electrodes 220. Stated another way, no plane perpendicular to the front and rear surfaces 113, 114 of the head 110 intersects more than one of the plurality of first and second electrodes 210, 220. Moving in a direction along the longitudinal axis from the proximal end 111 of the head 110 to the distal end 112 of the head 110, the first and second electrodes 210, 220 are positioned in an alternating arrangement.

In the exemplified embodiment, a portion of each of the first electrodes 210 and a portion of each of the second electrodes 220 also extends onto the side surface 116 of the head 110. The portions of the first and second electrodes 210, 220 at least partially overlap in the axial direction on the side surface 116 of the head 110 such that a reference plane that is parallel to the front surface 113 of the head 110 intersects the portions of each of the first and second electrodes 210, 220. To explain a different way, the first electrode 210 terminates in a distal end 212 that is located closer to the rear surface 114 of the head 110 than a distal end 222 of the second electrode 210 (similarly the distal end 222 of the second electrode 220 is closer to the front surface 113 of the head 110 than the distal end 212 of the first electrode 210). Thus, although the first and second electrodes 210, 220 are axially spaced apart, they extend a sufficient distance onto the side surface 116 of the head 110 so that they overlap in the axial direction. This maintains the first and second electrodes 210, 220 sufficiently close together to ensure that saliva and/or toothpaste slurry will contact one of the first electrodes 210 and one of the second electrodes 220 while extending between the first and second electrodes 210, 220 to create an electric field as discussed herein.

Furthermore, as noted above the tooth cleaning element field 102 is bounded axially by the distal-most cleaning element 103 and the proximal-most cleaning element 104. In the exemplified embodiment, the first electrodes 210 and the second electrodes 220 are each located along a transverse reference plane that is located between the distal-most and proximal-most cleaning elements 103, 104 of the tooth cleaning element field 102. Thus, in the exemplified embodiment none of the first and second electrodes 210, 220 is positioned axially beyond the bounds of the tooth cleaning element field 102.

Figure 5:
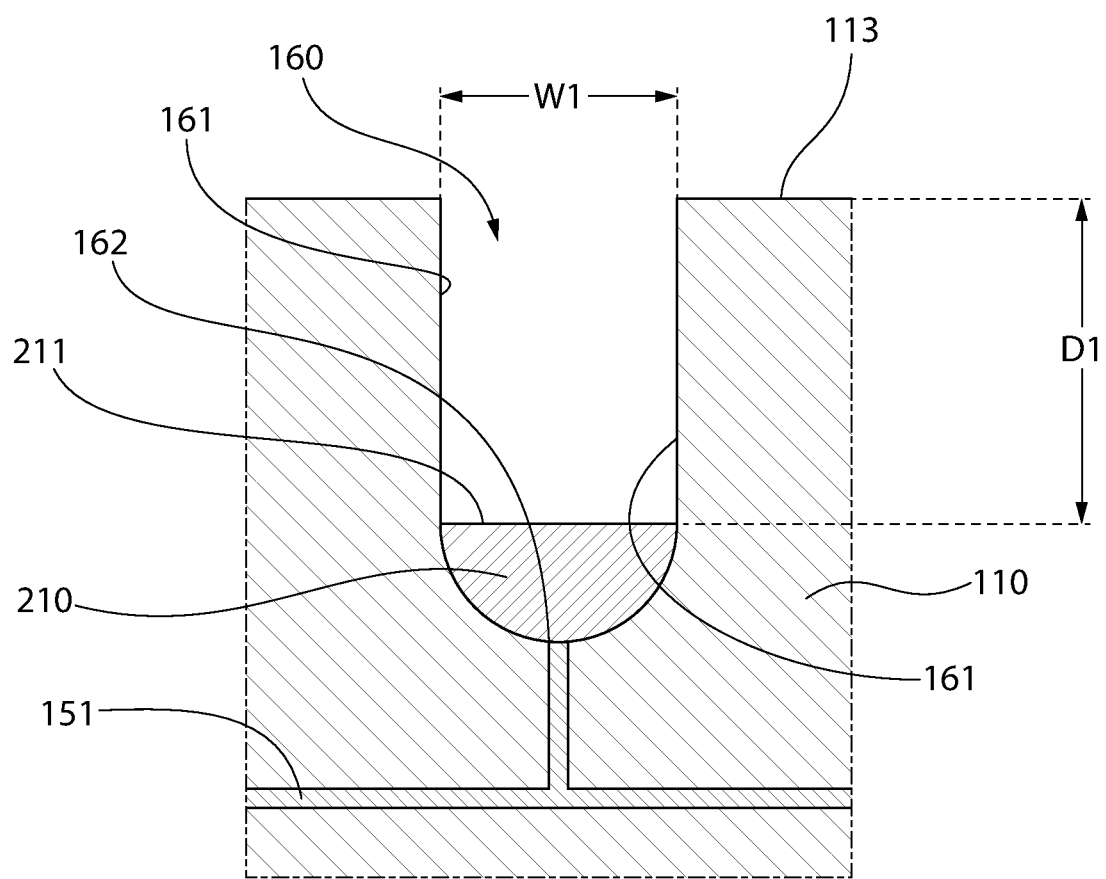
FIG. 5 is a close-up view of area V of FIG. 4B.

Referring to FIG. 5, one of the first depressions 160 with one of the first electrodes 210 therein is illustrated. The discussion of FIG. 5 is relevant to each of the first and second depressions 160, 170 when one of the first and second electrodes 210, 220 is positioned therein. Thus, although width and depth dimensions are provided below referring specifically to one of the first depressions 160 and one of the first electrodes 210, the description may be applicable to each of the first depressions 160 and first electrodes 210 and to each of the second depressions 170 and second electrodes 220.

In the exemplified embodiment, the first depression 160 has a first width W1. Furthermore, the exposed surface 211 of the first electrode 210 is recessed a first depth D1 from the exposed outer surface (i.e., the front surface 113) of the head 110. Stated another way, the first groove 165 has a first depth D1 measured from the front surface 113 of the head 110 to the floor of the first groove 165, which is formed by the exposed surface 211 of the first electrode 210. In the exemplified embodiment, the first depth D1 is equal to or greater than the first width W1. In some embodiments, the first depth D1 is greater than the first width W1. In some embodiments, the ratio of the first depth D1 to the first width W1 may be between 4:1 and 1:1, and more specifically between 3:1 and 1.5:1. By recessing the exposed surface 211 of the first electrode 210 a greater distance than the width W1 of the first depression 160, the likelihood of a user feeling an electric shock from the first electrode 210 is further decreased because it will be very difficult if not impossible for a user to directly contact his/her oral surfaces (inner cheek surfaces, tongue, gums, etc.) to the first electrode 161.

Figure 6:
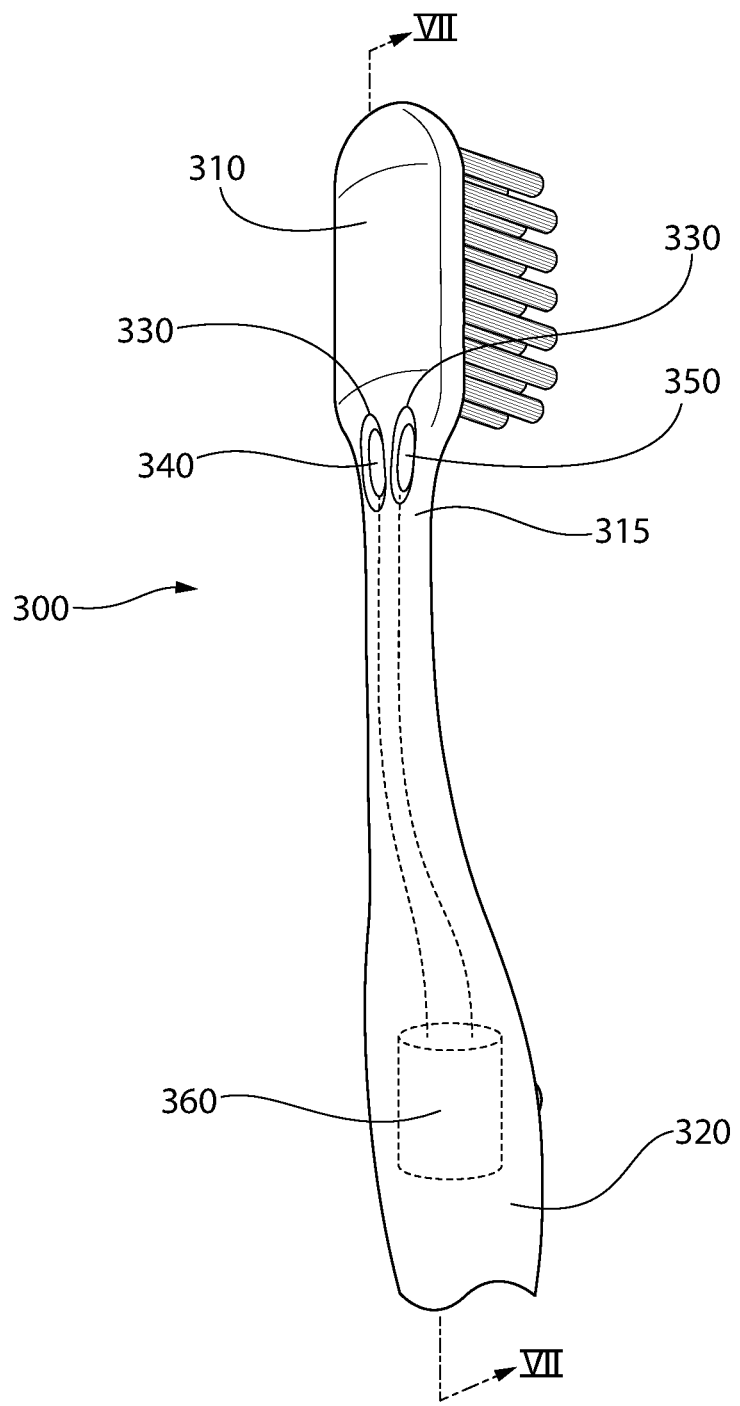
FIG. 6 is a rear perspective view of an oral care implement in accordance with a second embodiment of the present invention.
Figure 7:
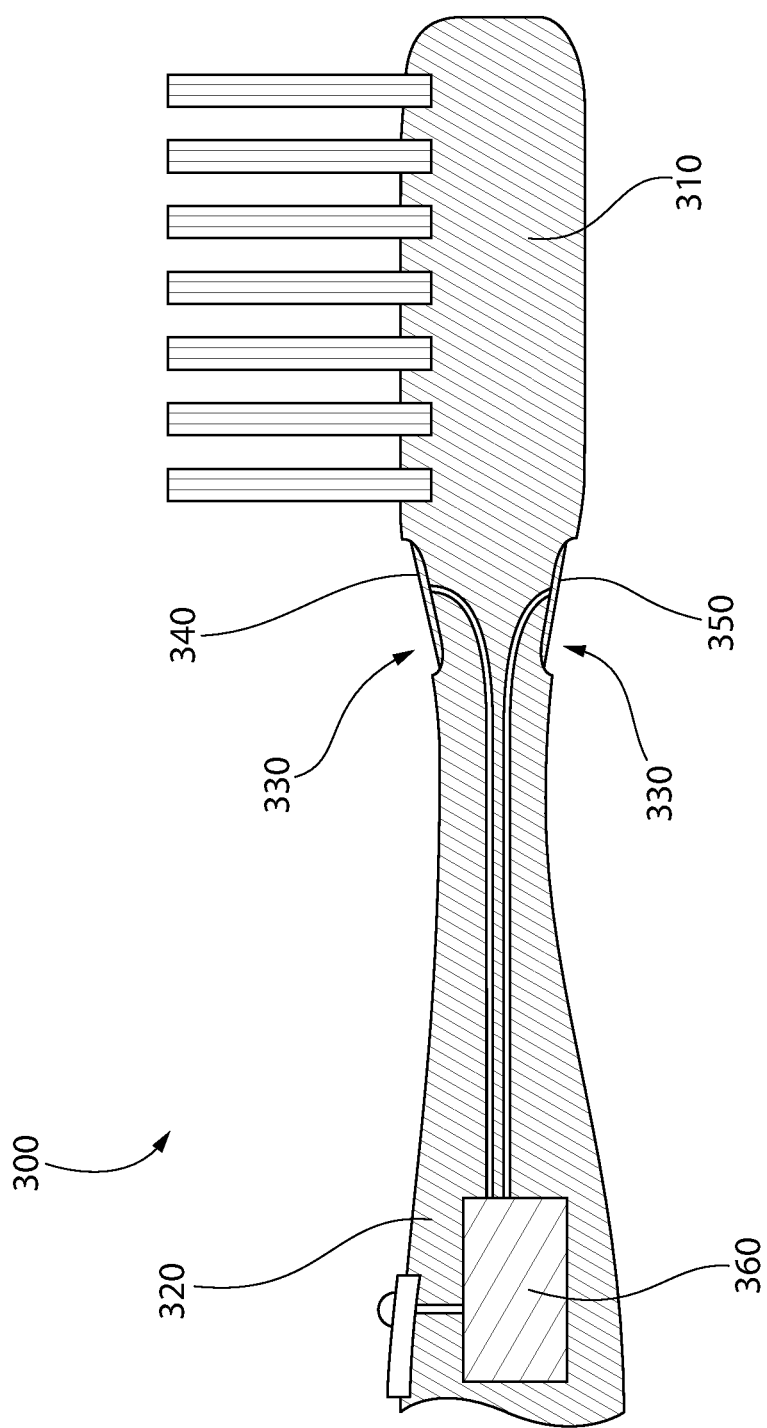
FIG. 7 is a cross-sectional view taken along line VII-VII of FIG. 6.

Referring to FIGS. 6 and 7 concurrently, an oral care implement 300 will be described in accordance with another embodiment of the present invention. Certain features of the oral care implement 300 are illustrated in the drawings but not described herein, it being understood that the description of the similar feature of the oral care implement 100 provided above is applicable. The oral care implement 300 generally comprises a head 310, a handle 320, and a neck 315 extending between the handle 320 and the head 310. In this embodiment, a plurality of depressions 330 are formed into the neck 315 of the oral care implement 300. Specifically, in this embodiment there are two depressions 330 formed into the rear surface of the neck 315 (visible in FIG. 6) and two depressions 330 formed into the front surface of the neck 315 (one of which is visible in FIG. 7). In other embodiments there may be two depressions 330 formed into one of the front or rear surfaces of the neck 315 only, there may be a single depression 330 formed into each of the front and rear surfaces of the neck 315, or the like.

One of a first electrode 340 and a second electrode 350 is positioned within each of the depressions 330. At least one, and possibly both, of the first and second electrodes 340, 350 may be a sacrificial electrode in some embodiments as described herein. The first and second electrodes 340, 350 are operably coupled to a power source 360 to have opposite electric charges similar to that which was described above. In the exemplified embodiment, there is provided one of the first electrodes 340 and one of the second electrodes 350 on each of the front and rear surfaces of the neck 315, the first and second electrodes 340, 350 having an opposite charge. However, in other embodiments all of the electrodes on the front surface of the neck 315 may have a first charge and all of the electrodes on the rear surface of the neck 315 may have a second charge that is opposite the first charge. Thus, variations in the type of electrode within each depression 330 are possible in various alternative embodiments. Because less saliva is present on the neck 315 of the oral care implement 300 during use than on the head 310, it may be beneficial in this embodiment to have one of each of the first and second electrodes 340, 350 on each of the front and rear surfaces of the neck 315 to ensure that the electrodes 340, 350 are sufficiently close together so that saliva will act as the electrolyte and close the circuit as discussed herein.

Each of the first electrodes 340 has an exposed surface 341 and each of the second electrodes 350 has an exposed surface 351. As with the previously described embodiment, in this embodiment the exposed surfaces 341, 351 of each of the first and second electrodes 340, 350 are recessed relative to the exposed outer surface of the neck 315. Thus, for the electrodes 340, 350 positioned on the front surface of the neck 315, the exposed surfaces 341, 351 of the electrodes 340, 350 are recessed relative to the front surface of the neck 315 and for the electrodes 340, 350 positioned on the rear surface of the neck 315, the exposed surfaces 341, 351 of the electrodes 340, 350 are recessed relative to the rear surface of the neck 315.

Figure 8:
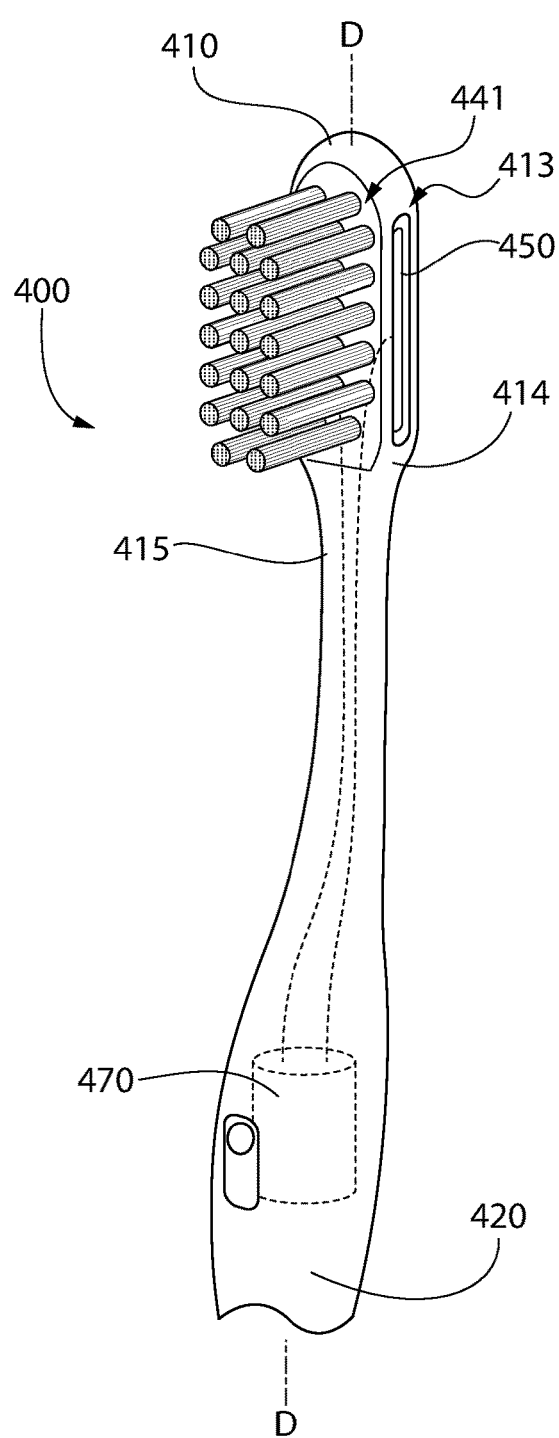
FIG. 8 is a front perspective view of an oral care implement in accordance with a third embodiment of the present invention.
Figure 9:
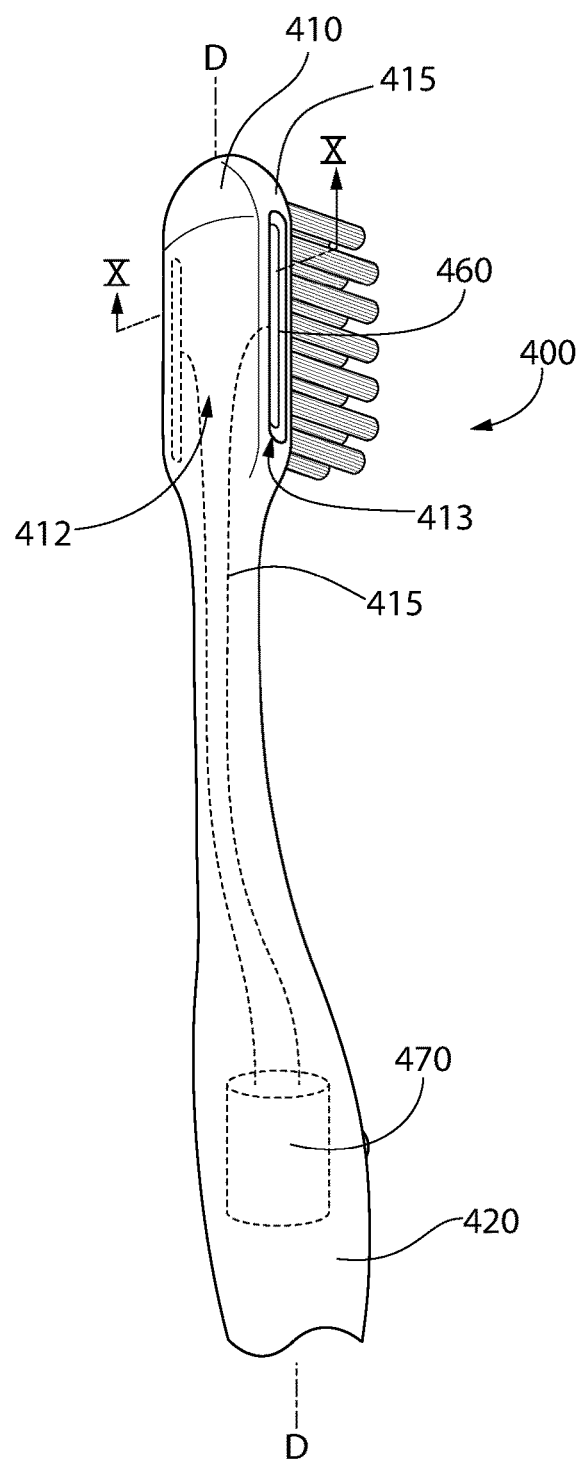
FIG. 9 is a rear perspective view of the oral care implement of FIG. 8.
Figure 10:
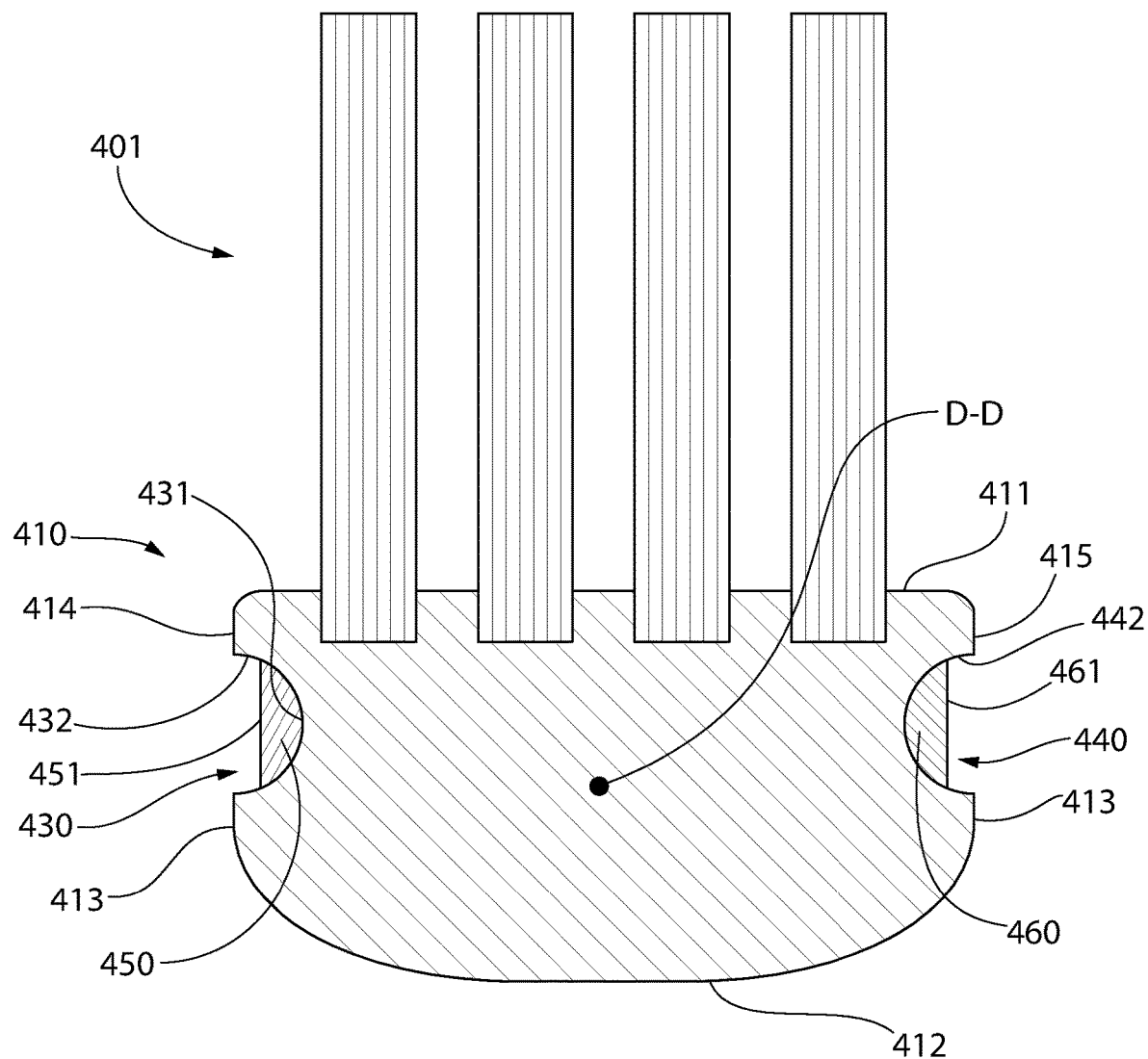
FIG. 10 is a cross-sectional view taken along line X-X of FIG. 9.

Referring to FIGS. 8-10 concurrently, an oral care implement 400 will be described in accordance with another embodiment of the present invention. Certain features of the oral care implement 400 are illustrated in the drawings but not described herein, it being understood that the description of the similar feature of the oral care implement 100 provided above is applicable. The oral care implement 400 generally comprises a head 410, a handle 420, and a neck 415 extending between the handle 420 and the head 410. The head 410 has an exposed outer surface that comprises a front surface 411, an opposite rear surface 412, and a side surface 413 extending between the front and rear surfaces 411, 412. Furthermore, the head 410 extends along a longitudinal axis D-D from a proximal end that is coupled to the handle 420 to a distal end. The side surface 413 of the head 410 comprises a first portion 414 located on a first side of the longitudinal axis A-A and a second portion 415 located on a second side of the longitudinal axis A-A.

In this embodiment, a first depression 430 is formed into the first portion 414 of the side surface 413 of the head 410 and a second depression 440 is formed into the second portion 415 of the side surface 413 of the head 410. The first depression 430 is defined by a floor 431 that is recessed relative to the first portion 414 of the side surface 413 of the head 410 and a sidewall 432 that extends from the floor 431 to the first portion 414 of the side surface 413 of the head 410. Similarly, the second depression 440 is defined by a floor 441 that is recessed relative to the second portion 415 of the side surface 413 of the head 410 and a sidewall 442 that extends from the floor 441 to the second portion 415 of the side surface 413 of the head 410. Each of the first and second depressions 430, 440 are formed by grooves that are formed directly into the side surface 413 of the head 410.

A first electrode 450 is positioned within the first depression 430 and a second electrode 460 is positioned within the second depression 440. At least one, and possibly both, of the first and second electrodes 450, 460 may be a sacrificial electrode in some embodiments as described herein. Each of the first and second electrodes 450, 460 is operably coupled to a power source 470 so that the first and second electrodes 450, 460 have opposite electrical charges (one of the first and second electrodes 450, 460 has a positive electric charge and the other of the first and second electrodes 450, 460 has a negative electric charge). The first electrode 450 is positioned within the first depression 430 so as to be in contact with the floor 431 and a portion of the sidewall 432 of the first depression 430. The second electrode 460 is positioned within the second depression 440 so as to be in contact with the floor 441 and a portion of the sidewall 442 of the second depression 440. However, the invention is not to be so limited and the first and second electrodes 450, 460 may be in contact with the floor 431, 441 of the first and second depressions 430, 440, respectively, but not also the sidewalls 432, 442. Furthermore, other arrangements are possible.

However, in the exemplified embodiment the first electrode 450 has an exposed surface 451 that is recessed relative to the first portion 414 of the side surface 413 of the head 410. Similarly, in the exemplified embodiment the second electrode 460 has an exposed surface 461 that is recessed relative to the second portion 415 of the side surface 413 of the head 410. Thus, the exposed surfaces 451, 461 of each of the first and second electrodes 450, 460 are recessed relative to the side surface 413 of the head 410 on which they are located. In certain embodiments, the depths of the first and second depressions 430, 440 measured from the side surface 413 of the head 410 to the exposed surface 451, 461 of the first and second electrodes 450,460 is greater than a width of the first and second depression 430, 440, as described above with reference to FIG. 5. This reduces the likelihood of a user's oral cavity surfaces contacting the first and second electrodes 450, 460 during use of the oral care implement 400.

In the exemplified embodiment, each of the first and second depressions 430, 440 is elongated in a direction of the longitudinal axis D-D along the respective portion 414, 415 of the side surface 413 of the head 410 into which it is formed. Furthermore, each of the first and second depressions 430, 440 terminates in an elongated opening in the respective portion 414, 415 of the side surface 413 of the head 410. The exact length of the first and second depression 430, 440 (and the first and second openings) is not to be limiting of the present invention in all embodiments although they may be elongated and extend a majority of a length of the head 410 in some embodiments.

It should be appreciated that in this embodiment the head 410 is not necessarily hollow, but rather it is preferably solid but merely includes the depressions 430, 440 are its opposite lateral sides. Thus, there is no passageway extending through the head 410 that connects the first and second depressions 430, 440, but rather the first and second depressions 430, 440 are discrete and separate depressions 430, 440 located on opposite sides of the head 410 that are separated transversely by the material of the head 410. Thus, the depressions 430, 440 are merely channels or grooves or elongated cut-outs formed into the side surface 413 of the head 410, each depression 430, 440 having its own floor and sidewalls as described herein and illustrated in the drawings.

Figure 11:
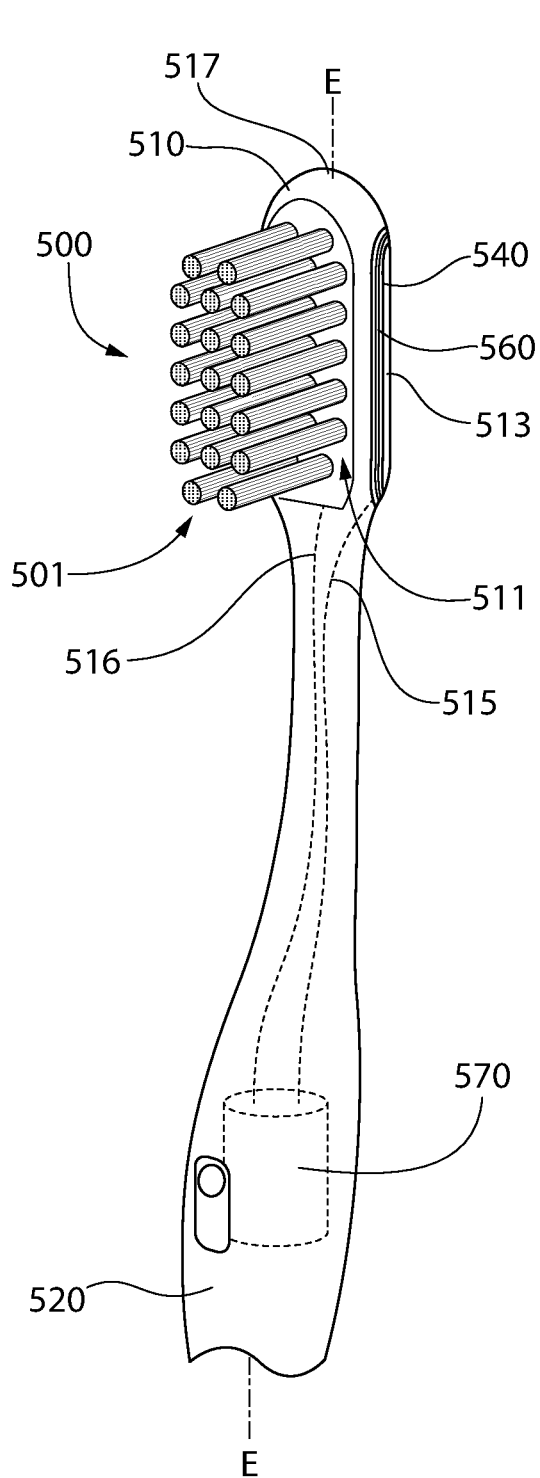
FIG. 11 is a front perspective view of an oral care implement in accordance with a fourth embodiment of the present invention.
Figure 12:
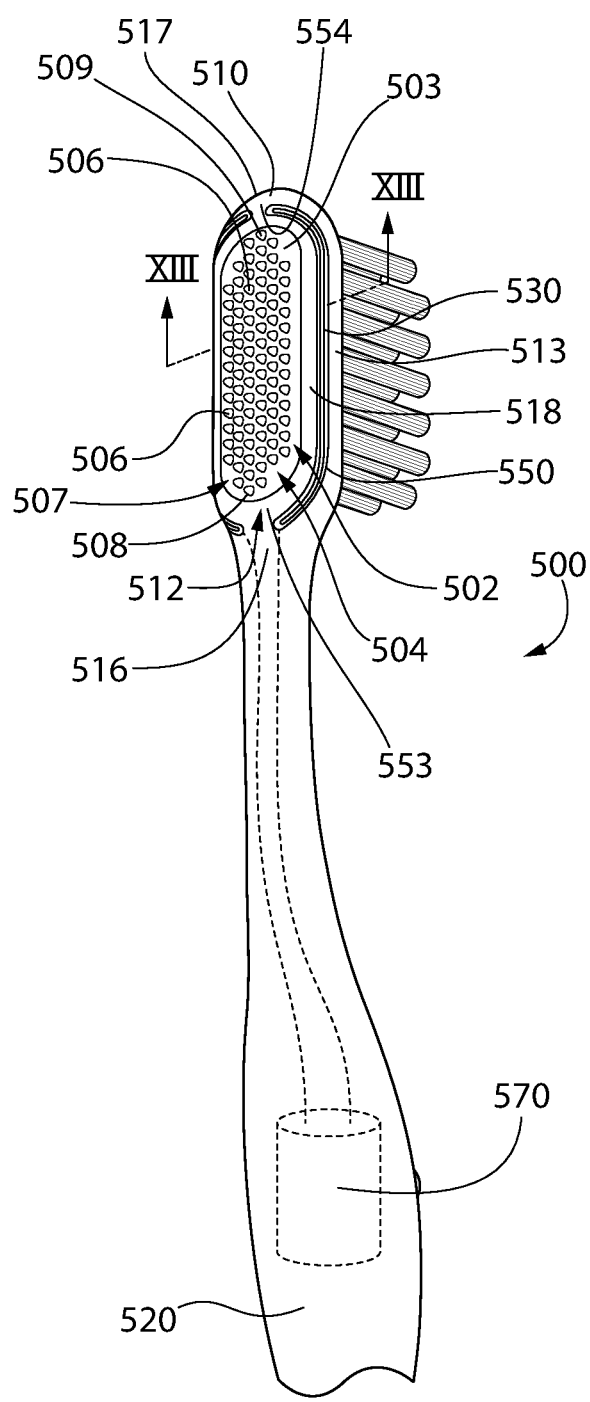
FIG. 12 is a rear perspective view of the oral care implement of FIG. 11.
Figure 13:
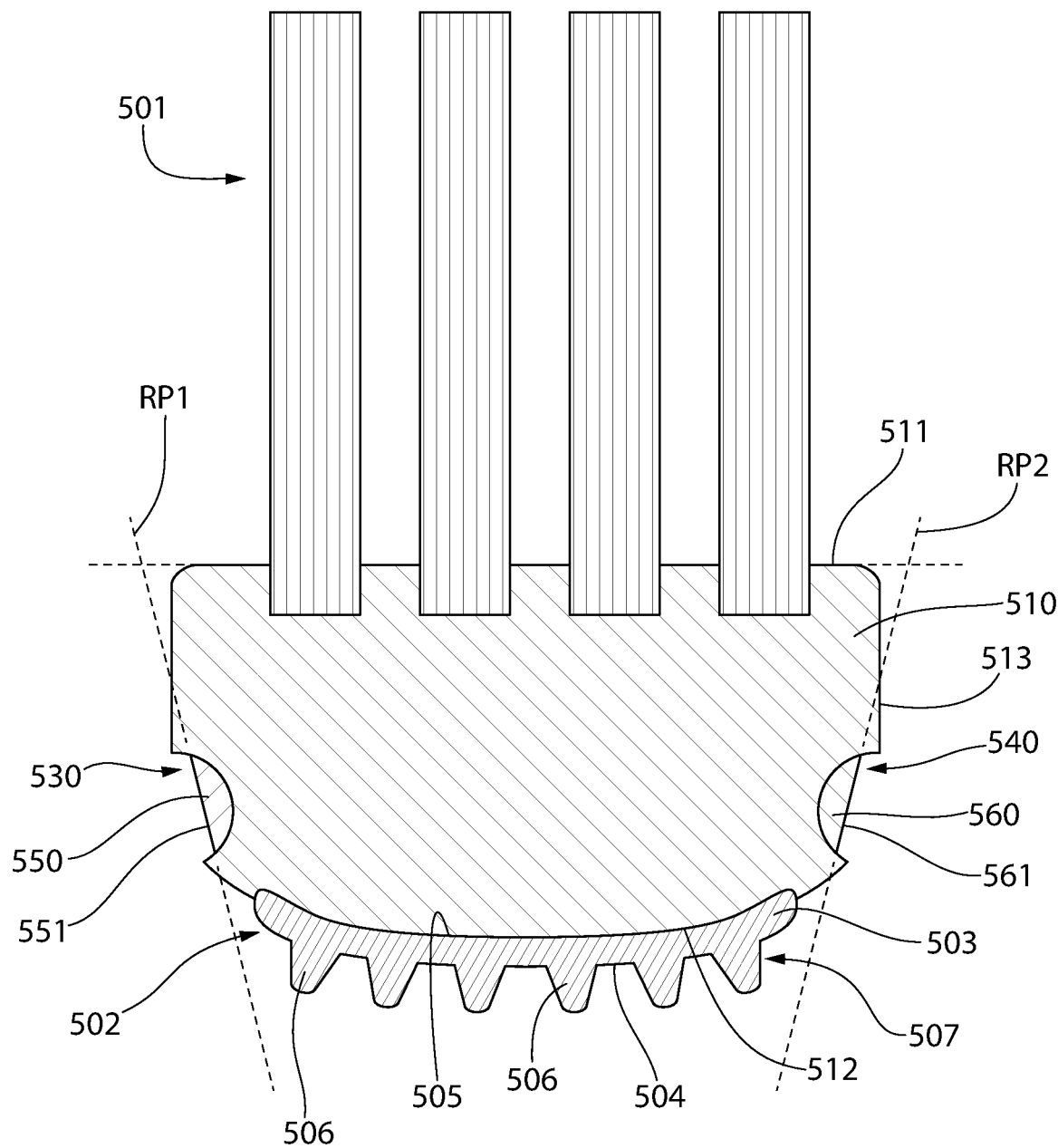
FIG. 13 is a cross-sectional view taken along line XIII-XIII of FIG. 12.
Figure 14:
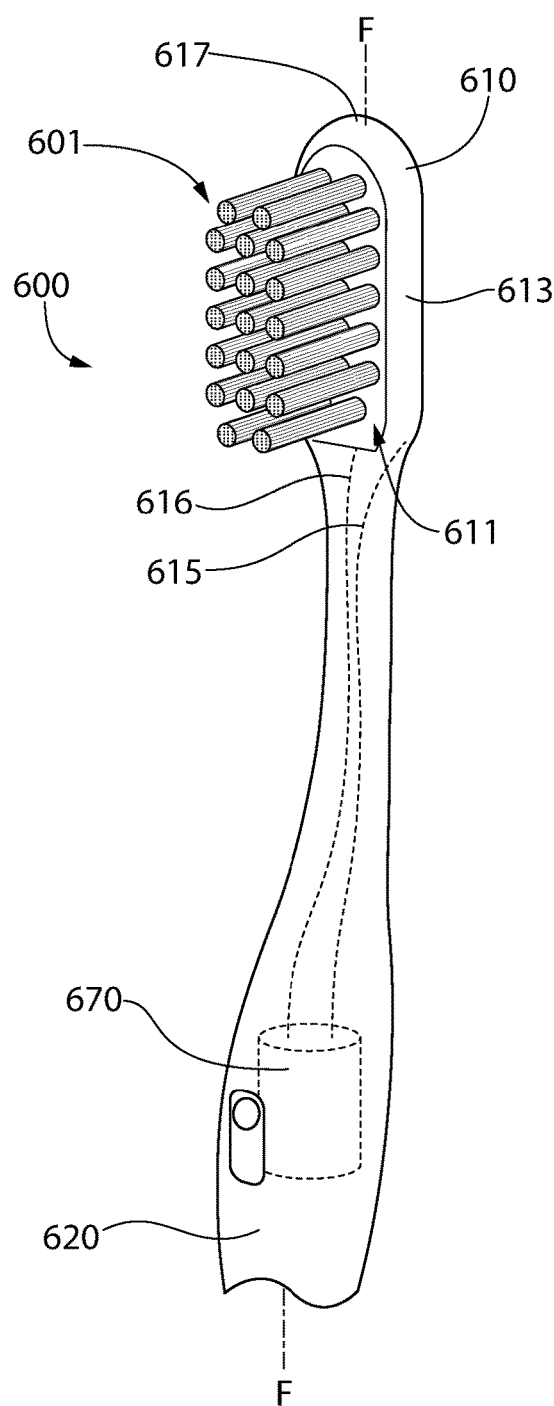
FIG. 14 is a front perspective view of an oral care implement in accordance with a fifth embodiment of the present invention.
Figure 15:
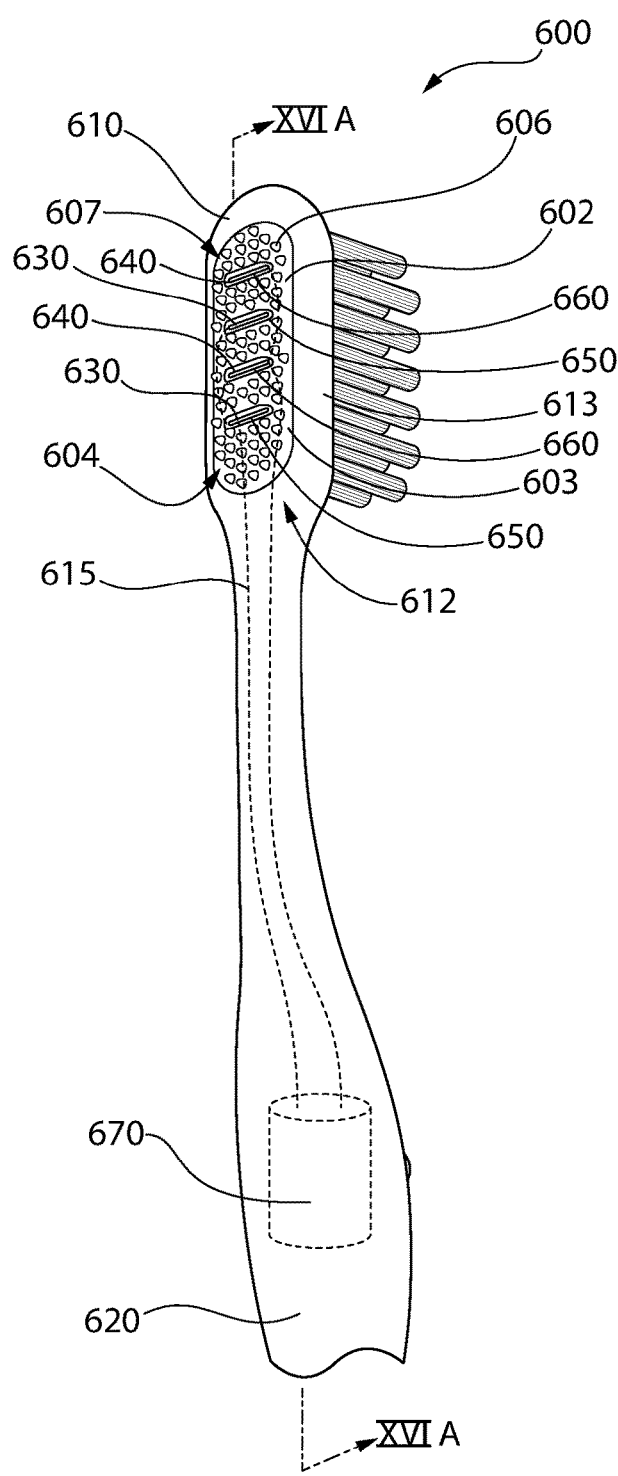
FIG. 15 is a rear perspective view of the oral care implement of FIG. 14

Referring to FIGS. 11-13 concurrently, an oral care implement 500 will be described in accordance with another embodiment of the present invention. Certain features of the oral care implement 500 are illustrated in the drawings but not described herein, it being understood that the description of the similar feature of the oral care implement 100 provided above is applicable. The oral care implement 500 generally comprises a head 510, a handle 520, and a neck 515 extending between the handle 520 and the head 510. The head 510 has an exposed outer surface that comprises a front surface 511, an opposite rear surface 512, and a side surface 513 extending between the front and rear surfaces 511, 512. Furthermore, the head 510 extends along a longitudinal axis E-E from a proximal end 516 that is coupled to the handle 520 to a distal end 517.

In this embodiment, a plurality of tooth cleaning elements 501 extend from the front surface 511 of the head 510 for cleaning a user's teeth and gums. The tooth cleaning elements 501 may be any type of tooth cleaning element as described herein above and may be secured to the head 510 using any technique now known or later discovered. Furthermore, in this embodiment a soft tissue cleaner 502 is provided on the rear surface 512 of the head 510. The soft tissue cleaner 502 may comprise a pad portion 503 and a plurality of protuberances 506 extending from the pad portion 503. Specifically, the pad portion 503 comprises an exposed upper surface 504 and an opposite lower surface 505 that is in contact with the rear surface 512 of the head 510. The plurality of protuberances 506 extend from the upper surface 504 of the pad portion 503 and are exposed for direct contact with the user's oral cavity and tongue during use of the oral care implement 500. The soft tissue cleaner 502 may be formed of an elastomeric material such as a thermoplastic elastomer and it may be injection molded onto the rear surface 512 of the head 510. The soft tissue cleaner 502 may be injected molded into a basin-like cavity formed into the rear surface 512 of the head 510, or it may be injection molded directly onto the outermost part of the rear surface 512 of the head 510.

In this embodiment the soft tissue cleaner 502 comprises a protuberance field 507. The protuberance field 507 is the region of the soft tissue cleaner 502 that is bounded by the outer-most ones of the protuberances 506. Thus, the protuberance field 507 is the region of the soft tissue cleaner 502 that has the protuberances 506 thereon.

Furthermore, in this embodiment the oral care implement 500 comprises a first electrode 550 and a second electrode 560, each of which is operably coupled to a power source 570 to have an opposite electrical charge. Thus, one of the first and second electrodes 550, 560 has a positive electrical charge while the other one of the first and second electrodes 550, 560 has a negative electrical charge. At least one, and possibly both, of the first and second electrodes 550, 560 may be a sacrificial electrode in some embodiments as described herein. As best seen in FIG. 13, the first electrode 550 is disposed within a first depression 530 formed into the head 510 and the second electrode 560 is disposed within a second depression 540 formed into the head 510. As with the previously described embodiments, an exposed surface 551 of the first electrode 550 and an exposed surface 561 of the second electrode 560 are recessed relative to the rear surface 512 of the head 510. Although recessing the first and second electrodes 550, 560 relative to the rear surface 512 of the head 510 is shown in the drawings, it is not necessarily required in this embodiment.

In this embodiment, the first and second electrodes 550, 560 substantially surround the protuberance field 507. More specifically, in this embodiment the first and second electrodes 550, 560 collectively surround the soft tissue cleaner 502 and the protuberance field 507. Thus, each of the first and second electrodes 550, 560 is positioned around a portion of the soft tissue cleaner 507 so that collectively the first and second electrodes 550, 560 substantially surround the soft tissue cleaner 502. In that regard, in the exemplified embodiment each of the first and second electrodes 550, 560 is positioned on the rear surface 512 of the head 510 and they may extend partially onto the side surface 513 of the head 510 as well. In some embodiments the soft tissue cleaner 502 may take up a majority or the entirety of the rear surface 512 of the head 510, and in such instances the first and second electrodes 550, 560 may be located mostly or entirely on the side surface 513 of the head 510. The first electrode 550 is located on the rear surface 512 of the head 510 on a first side of the longitudinal axis E-E and the second electrode 560 is located on the rear surface 512 of the head 510 on a second side of the longitudinal axis E-E that is opposite the first side of the longitudinal axis E-E. The first electrode 550 is adjacent to the soft tissue cleaner 502 on a first side of the soft tissue cleaner 502 and the second electrode 560 is adjacent to the soft tissue cleaner 502 on a second side of the soft tissue cleaner 502. In the exemplified embodiment, each of the first and second electrodes 550, 560 are substantially C-shaped, although the invention is not to be so limited in all embodiments.

The protuberance field 507 extends from a first end 508 to a second end 509 along the longitudinal axis E-E. Furthermore, each of the first and second electrodes 550, 560 extend axially beyond both the first and second ends 508, 509 of the protuberance field 507.

Although the first and second electrodes 550, 560 substantially surround the soft tissue cleaner 502, they are also spaced apart from one another. In that regard, in the exemplified embodiment the first and second electrodes 550, 560 are spaced apart by a first gap 553 located on the longitudinal axis E-E adjacent the proximal end 516 of the head 510 and a second gap 554 located on the longitudinal axis E-E adjacent the distal end 517 of the head 510. Thus, it is the first and second electrodes 550, 560 substantially surround the soft tissue cleaner 502 due to the existence of the first and second gaps 553, 554, which are necessary because the first and second electrodes 550, 560 must be maintained in a spaced apart manner for an electric field to be generated as described herein.

Although in the exemplified embodiment the first and second electrodes 550, 560 are illustrated wrapping around the distal and proximal ends of the soft tissue cleaner 502, this is not required in all embodiments. In some embodiments the first electrode 550 may be positioned on a first side of the soft tissue cleaner 502 while the second electrode 560 is positioned on a second opposite side of the soft tissue cleaner 502. In such an embodiment, each of the first and second electrodes 550, 560 may be elongated in a direction of the longitudinal axis E-E without having a curved portion that wraps around the soft tissue cleaner 502. In still other embodiments, each of the first and second electrodes 550, 560 may by itself substantially surround the soft tissue cleaner 502, such that the first and second electrodes 550, 560 are positioned in a concentric arrangement. Thus, modifications in the exact shape of the first and second electrodes 550, 560 are possible within the scope of the invention described herein.

Furthermore, in the exemplified embodiment the first and second electrodes 550, 560 are each spaced apart from the pad 503 of the soft tissue cleaner 502 by a portion of the exposed outer surface of the head 510. Thus, the soft tissue cleaner 502 is spaced apart from each of the first and second electrodes 550, 560. More specifically, an annular portion 518 of the outer surface of the head 510 separates each of the first and second electrodes 550, 560 from the soft tissue cleaner 502. Although in the exemplified embodiment the first and second electrodes 550, 560 are located adjacent to but not on (i.e., spaced apart from) the pad portion 503 of the soft tissue cleaner 502, in other embodiments the first and second electrodes 550, 560 may be located directly on a peripheral/perimeter region of the pad portion 503 of the soft tissue cleaner 502 so as to surround the protuberance field 507. Thus, the first and second electrodes 550, 560 would still collectively surround the protuberance field 507, but they would not surround the pad portion 503 of the soft tissue cleaner 502 because they would be located on the perimeter region of the pad portion 503.

In the exemplified embodiment, the exposed surfaces 551, 561 of the first and second electrodes 550, 560 are oriented at an oblique angle relative to the front and rear surfaces 511, 512 of the head 510. Stated another way, the exposed surface 551 of the first electrode 550 is located on a first reference plane RP1 that is oblique to the front surface 511 of the head 510 and the exposed surface 561 of the second electrode 560 is located on a second reference plane RP2 that is oblique to the front surface 511 of the head 510. The first and second reference planes RP1, RP2 are oriented so as to diverge with increasing distance from the front surface 511 of the head 510 in a direction opposite the rear surface 512 of the head 510 and converge with increasing distance from the rear surface 512 of the head 510 in a direction opposite the front surface 511 of the head 510. Of course, the orientation of the exposed surfaces 551, 561 of the first and second electrodes 550, 560 is not to be limiting of the present invention in all embodiments.

Referring to FIGS. 14-16A, an oral care implement 600 will be described in accordance with yet another embodiment of the present invention. Certain features of the oral care implement 600 are illustrated in the drawings but not described herein, it being understood that the description of the similar feature of the oral care implement 100 provided above is applicable. The oral care implement 600 generally comprises a head 610, a handle 620, and a neck 615 extending between the handle 620 and the head 610. The head 610 has an exposed outer surface that comprises a front surface 611, an opposite rear surface 612, and a side surface 613 extending between the front and rear surfaces 611, 612. Furthermore, the head 610 extends along a longitudinal axis F-F from a proximal end 616 that is coupled to the handle 620 to a distal end 617.

The oral care implement 600 comprises a plurality of tooth cleaning elements 601 extending from the front surface 611 of the head 610. The tooth cleaning elements 601 may be any type of tooth cleaning element as has been described herein above. The tooth cleaning elements 601 may be secured to the head 610 using any technique now known or later discovered. Furthermore, in this embodiment a soft tissue cleaner 602 is coupled to the rear surface 612 of the head 610. The soft tissue cleaner 602 may comprise a pad portion 603 and a plurality of protuberances 606 extending from the pad portion 603. Specifically, the pad portion 603 comprises an exposed upper surface 604 and an opposite lower surface 605 that is in contact with the rear surface 612 of the head 610. The plurality of protuberances 606 extend from the upper surface 604 of the pad portion 603 and are exposed for direct contact with the user's oral cavity and tongue during use of the oral care implement 600. The plurality of protuberances 606 collectively define a protuberance field 607 such that the protuberance field 607 that is bounded by the outer-most ones of the protuberances 606.

The protuberances 606 are nub-like elements that extend from the upper surface 604 of the pad portion 603 of the soft tissue cleaner 602. The nub-like elements are arranged on the pad portion 603 of the tissue cleaner 602 in a spaced apart manner and they may be arranged in aligned rows, aligned columns, or in a random array. In the exemplified embodiment, the protuberances are in the shape of a cone and they taper to a pointed tip. However, the invention is not to be so limited and the protuberances 606 may be rounded in other embodiments and may have more of a semi-spherical shape. Furthermore, in still other embodiments the protuberances 606 may include ridges extending across the pad portion 603 of the soft tissue cleaner 602. Thus, the invention is not to be limited by the structure and shape of the protuberances 606 in all embodiments, but rather the protuberances 606 may be any element that protrudes from the upper surface 604 of the pad portion 603 for direct engagement with a user's oral cavity surfaces. Although not mentioned above, this description of the protuberances 606 is also applicable to the protuberances 506 and any other soft tissue cleaner protuberances described herein.

The soft tissue cleaner 602 (including both the pad portion 603 and the protuberances 606) may be formed of an elastomeric material such as a thermoplastic elastomer and it may be injection molded onto the rear surface 612 of the head 610. The soft tissue cleaner 502 may be injected molded into a basin-like cavity formed into the rear surface 612 of the head 610 (discussed in more detail below with reference to FIG. 16B), or it may be injection molded directly onto the outermost part of the rear surface 612 of the head 610. In other embodiments, the soft tissue cleaner 502 may be formed separately from the head 610 and then later coupled to the head 610 using mechanical or chemical means.

The oral care implement 600 also comprises a first electrode 650 and a second electrode 660, each of which is operably coupled to a power source 670 to have an opposite electrical charge. In the exemplified embodiment, the oral care implement 600 has two of the first electrodes 650 and two of the second electrodes 660. Each of the first electrodes 650 has the same electrical charge (i.e., positive or negative) and each of the second electrodes 660 has the same electrical charge (i.e., positive or negative) such that each of the first electrodes 650 has the same electrical charge that is opposite to the electrical charge of each of the second electrodes 660. In this embodiment, the first and second electrodes 650, 660 are positioned on the rear surface 612 of the head 610, and more specifically within the protuberance field 607 of the soft tissue cleaner 602, in an alternating arrangement in a direction of the longitudinal axis F-F. Thus, whereas with the oral care implement 500 the first and second electrodes 550, 560 surrounded the protuberance field 507 and the soft tissue cleaner 502, in this embodiment the first and second electrodes 650, 660 are located within the protuberance field 607 of the soft tissue cleaner 602. In the exemplified embodiment, each of the first electrodes 650 is axially adjacent to one of the second electrodes 660 and vice versa. In certain embodiments, at least one of the first and second electrodes 650, 660 may be a sacrificial electrode. Furthermore, in some embodiments both of the first and second electrodes 650, 660 may be sacrificial electrodes.

As noted above, in this embodiment each of the first and second electrodes 650, 660 is at least partially, and preferably entirely located within the protuberance field 607 of the soft tissue cleaner 602. In the exemplified embodiment, a first depression 630 and a second depression 640 are formed into the upper surface 604 of the pad portion 603 of the soft tissue cleaner 602. Each of the first electrodes 650 is positioned within one of the first depressions 630 and each of the second electrodes 660 is positioned within one of the second depressions 640. In the exemplified embodiment, each of the first and second depressions 630, 640 are elongated in a direction transverse to the longitudinal axis F-F. However, the invention is not to be so limited and the first and/or second depressions 630, 640 may be elongated in a direction oblique or parallel to the longitudinal axis F-F in other embodiments. Furthermore, the first and/or second depressions 630, 640 may be annular or formed in the shape of a closed-geometry polygon in other embodiments. In some embodiments, the first and second depressions may be arranged as concentric circles. Thus, the exact structural embodiment of the first and second depressions 630, 640 (and hence also of the first and second electrodes 650, 660 that are positioned within the first and second depressions 630, 640) is not to be limiting of the present invention in all embodiments.

In this embodiment the depressions 630, 640 are grooves that are formed directly into the pad portion 603 of the soft tissue cleaner 602. Thus, the depressions 630, 640 comprise a floor and sidewalls much like the depressions discussed previously in this document, the difference being that the depressions 630, 640 are formed into the pad portion 603 of the soft tissue cleaner 602 rather than directly onto the head 610 of the oral care implement 600.

Figure 16A:
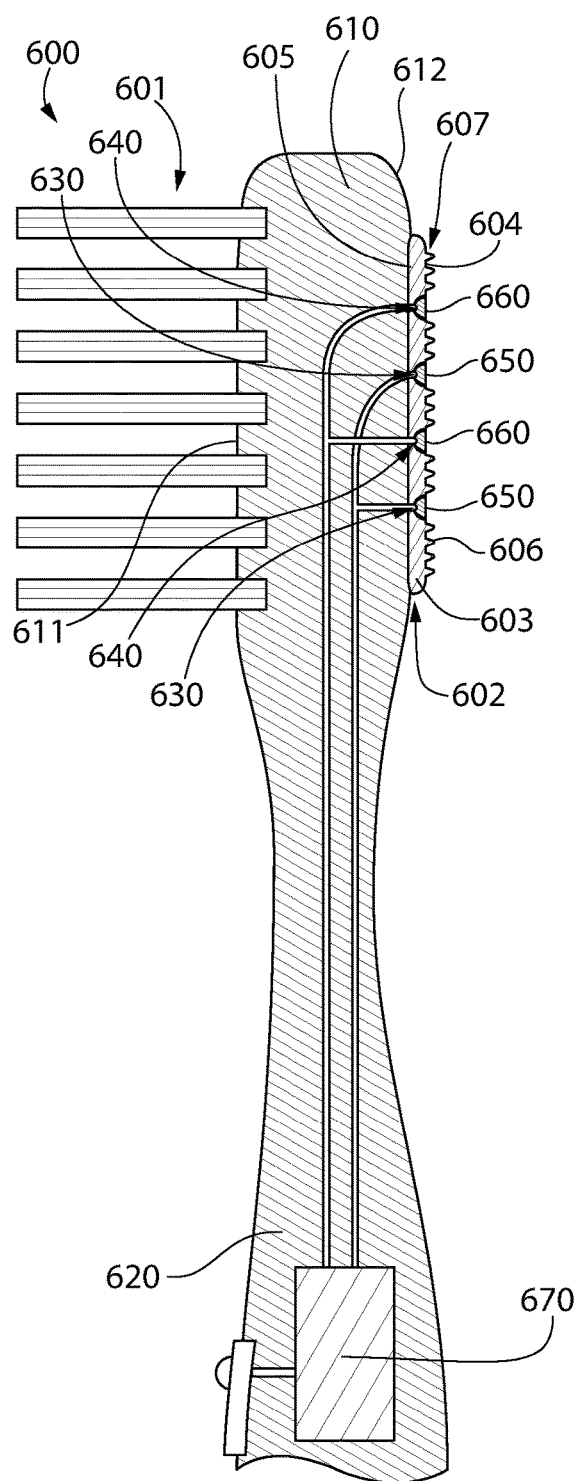
FIG. 16A is a cross-sectional view taken along line XVIA-XVIA of FIG. 15 in accordance with one embodiment.

As best seen in FIG. 16A, in the exemplified embodiment the first electrodes 650 have an exposed surface 651 and the second electrodes 660 have an exposed surface 661. In the exemplified embodiment, the exposed surfaces 651 of the first electrodes 650 and the exposed surfaces 661 of the second electrodes 660 are flush with the upper surface 604 of the pad portion 603 of the soft tissue cleaner 602. However, the invention is not to be so limited in all embodiments and in other embodiments the exposed surfaces 651, 661 of the first and second electrodes 650, 660 may be recessed relative to the upper surface 604 of the pad portion 603 of the soft tissue cleaner 602.

In still other embodiments, the exposed surfaces 651, 661 of the first and second electrodes 650, 660 may protrude beyond the upper surface 604 of the pad portion 603 of the soft tissue cleaner 602 while remaining recessed relative to the distal ends of the protuberances 606. For example, referring to FIG. 16B an alternative arrangement of the first and second electrodes 650, 660 on the soft tissue cleaner 602 is illustrated. Specifically, in this embodiment there are no depressions formed into the soft tissue cleaner 602 for retaining the first and second electrodes 650, 660. Rather, in this embodiment the first and second electrodes 650, 660 are positioned directly atop the upper surface 604 of the pad portion 603 of the soft tissue cleaner 602. Thus, the first and second electrodes 650, 660 are not recessed relative to or flush with the upper surface 604 of the pad portion 603 of the soft tissue cleaner 602, but rather they protrude from the upper surface 604 of the pad portion 603 of the soft tissue cleaner 602. Nonetheless, the exposed surfaces 651, 661 of the first and second electrodes 650, 660 are recessed relative to the distal ends 608 of the protuberances 606. As a result, direct contact between the user's oral cavity surfaces and the first and second electrodes 650, 660 can be prevented.

Figure 16B:
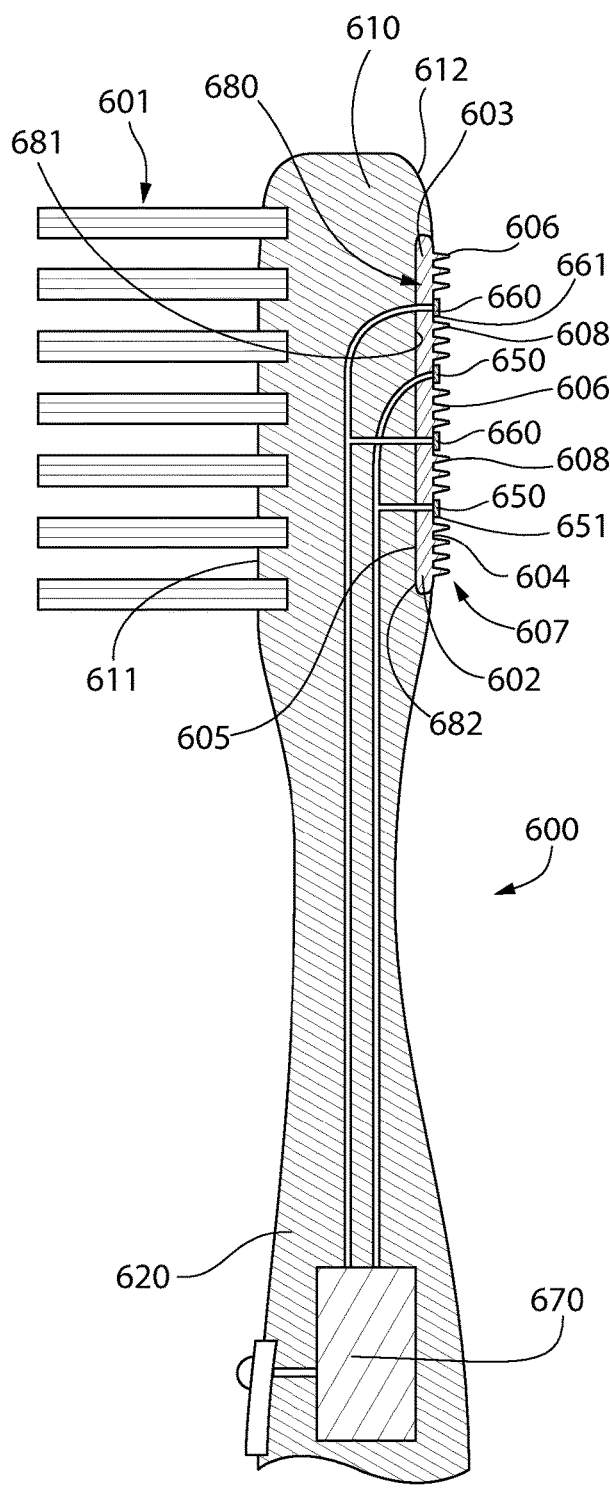
FIG. 16B is a cross-sectional view taken along line XVIA-XVIA of FIG. 15 in accordance with another embodiment.
Figure 17:
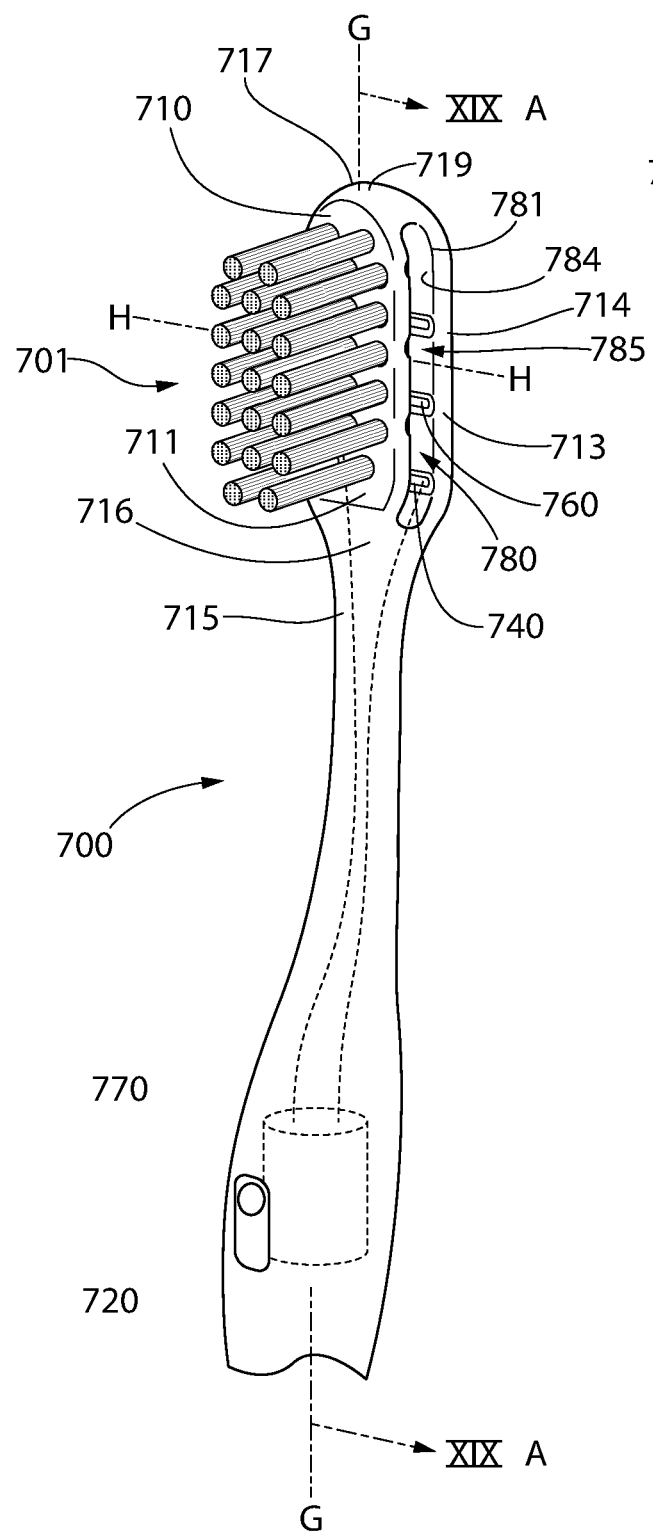
FIG. 17 is a front perspective view of an oral care implement in accordance with a sixth embodiment of the present invention.
Figure 18:
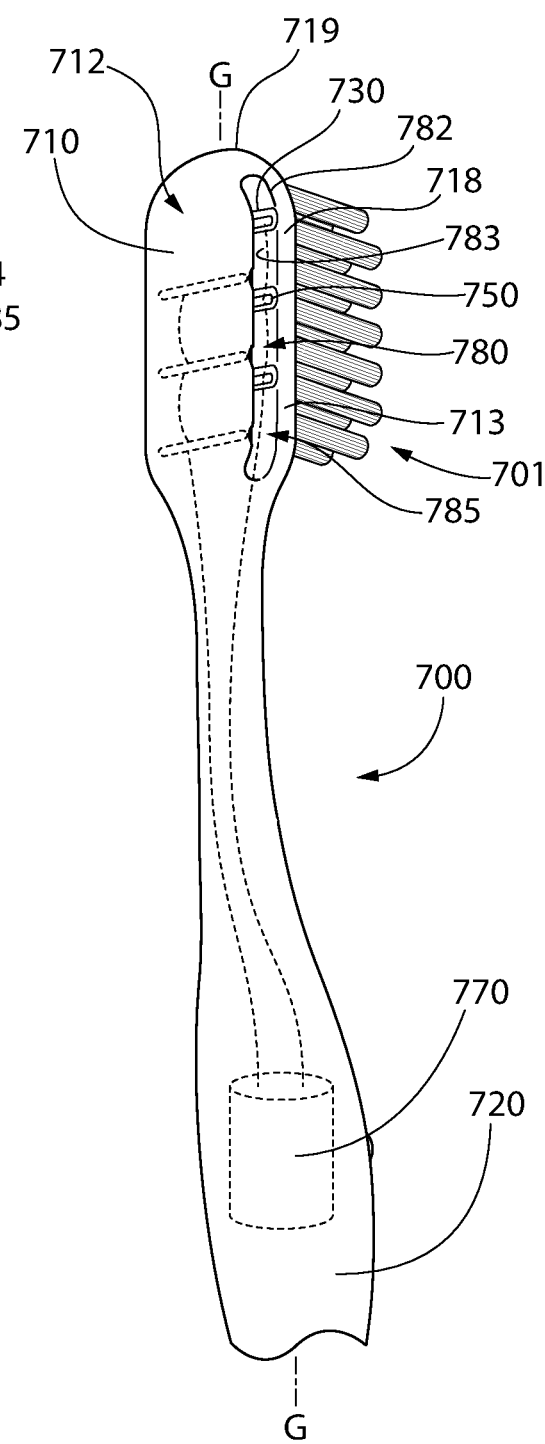
FIG. 18 is a rear perspective view of the oral care implement of FIG. 17.

Furthermore, in the embodiment of FIG. 16B, the rear surface 612 of the head 610 has a basin 680 formed therein. The basin 680 has a floor 681 and sidewalls 682 extending from the floor 681 to the rear surface 612 of the head 610. In this embodiment, the soft tissue cleaner 602 is located within the basin 680 so that the upper surface 604 of the pad portion 603 of the soft tissue cleaner 602 is flush with the rear surface 612 of the head 610. This is different from the embodiment of FIG. 16A where the soft tissue cleaner 602 is merely positioned on the rear surface 612 of the head 610 and not within any basin or cavity formed therein. Various combinations of the embodiments shown in FIGS. 16A and 16B are possible. For example, the pad portion 603 of the soft tissue cleaner 602 may be positioned within a basin as shown in FIG. 16B and the electrodes 650, 660 may be positioned within depressions 630, 640 formed into the upper surface 604 of the pad portion 603 of the soft tissue cleaner 602 as shown in FIG. 16A. Thus, different permutations of these embodiments are possible as would be appreciated by persons skilled in the art.

Referring now to FIGS. 17-19A, an oral care implement 700 will be described in accordance with another embodiment of the present invention. Certain features of the oral care implement 700 are illustrated in the drawings but not described herein, it being understood that the description of the similar feature of the oral care implement 100 provided above is applicable. The oral care implement 700 generally comprises a head 710, a handle 720, and a neck 715 extending between the handle 720 and the head 710. The head 710 has an exposed outer surface that comprises a front surface 711, an opposite rear surface 712, and a side surface 713 extending between the front and rear surfaces 711, 712. Furthermore, the head 710 extends along a longitudinal axis G-G from a proximal end 716 that is coupled to the handle 720 to a distal end 717. A plurality of tooth cleaning elements 701 are coupled to the head 710 to extend from the front surface 711 of the head 700. Although not illustrated, a soft tissue cleaner may be coupled to the rear surface 712 of the head 710 as described above.

In this embodiment, the oral care implement 700 comprises a through-hole 780 extending through the head 710 from a first opening 781 in the side surface 713 of the head 710 to a second opening 782 in the side surface 713 of the head 710. Each of the first and second openings 781, 782 is elongated in a direction of the longitudinal axis G-G. In the exemplified embodiment, the first opening 781 and the second opening 782 extend along a substantial entirety of an axial length of the head 710. Thus, the head 710 has openings 781, 782 in its opposing side surfaces and a through-hole 780 extending between the openings 781, 782 that create a transverse passageway extending along a majority of the length of the head 710.

In the exemplified embodiment the through-hole 780 extends along an axis H-H that is transverse to the longitudinal axis G-G. Specifically, the side surface 713 of the head 710 comprises a first lateral portion 714 on a first side of the longitudinal axis G-G, a second lateral portion 718 on a second side of the longitudinal axis G-G that is opposite the first side of the longitudinal axis G-G, and a distal portion 719 extending between the first and second lateral portions 714, 718. The distal portion 719 of the side surface 713 comprises the distal end 717 of the head 710. The first opening 781 is formed into the first lateral portion 714 of the side surface 713 of the head 710 and the second opening 782 is formed into the second lateral portion 718 of the side surface 713 of the head 710. Of course, the invention is not to be so limited in all embodiments and in other embodiments the first opening 781 may be located in one of the first and second lateral portions 714, 718 of the side surface 713 while the second opening 782 is located in the distal portion 719 of the side surface 713. Thus, the through-hole 780 may be oblique rather than transverse to the longitudinal axis G-G.

In the exemplified embodiment, each of the first and second openings 781, 782 is elongated in a direction of the longitudinal axis G-G of the head 710 such that they extend along substantially the entirety of the first and second lateral portions 714, 718 of the side surface 713 of the head 710, respectively. Of course, the first and second openings 781, 782 may be reduced in length in other embodiments. In any event, the through-hole 780 forms a passageway 785 through the head 710 that is bounded by an upper surface 783 and a lower surface 784. In the exemplified embodiment, there is no barrier between the first and second openings 781, 782 and the passageway 785 formed by the through-hole 780 is a continuous, unimpeded passageway 785 extending transversely through the head 710 of the oral care implement 700 from the first opening 781 to the second opening 782. In alternative embodiments, a barrier element may be provided within the passageway 785 between the upper and lower surfaces 783, 784 as discussed briefly below.

In this embodiment, the oral care implement 700 comprises a plurality of first electrodes 750 on the upper surface 783 of the passageway 785 and a plurality of second electrodes 760 on the lower surface 784 of the passageway 785. Although three of the first electrodes 750 and three of the second electrodes 760 are illustrated in the exemplified embodiment, there could be just a single one of each of the first and second electrodes 750, 760 or any number of electrodes as desired. Each of the first and second electrodes 750, 760 is operably coupled to a power source 770 (located on the handle 720 or elsewhere as described herein) so that the first electrodes 750 and the second electrodes 760 have opposite electrical charges (i.e., one of the first and second electrodes 750, 760 may be an anode and the other of the first and second electrodes 750, 760 may be a cathode). In certain embodiments, at least one or both of the first and second electrodes 750, 760 may be a sacrificial electrode, the details of which have been described herein above.

In the exemplified embodiment, a plurality of first depressions 730 are formed into the upper surface 783 of the passageway 785 and a plurality of second depressions 740 are formed into the lower surface 784 of the passageway 785. Each of the first and second depressions 730, 740 is defined by a floor and a sidewall as described above with regard to the previously described embodiments. Each of the first electrodes 750 is positioned within one of the first depressions 730 and each of the second electrodes 760 is positioned within one of the second depressions 740. In the exemplified embodiment, each of the first and second depressions 730, 740 (and hence also each of the first and second electrodes 750, 760) is elongated and extends in a direction generally transverse to the longitudinal axis G-G. However, the invention is not to be so limited in all embodiments and the depressions 730, 740 and electrodes 750, 760 may be oriented oblique or parallel to the longitudinal axis G-G, or they may be arranged in any other manner as has been described throughout this document. Furthermore, either a single electrode or multiple electrodes may be positioned within each of the first and second depression 730, 740.

In some embodiments the depressions 730, 740 may be omitted and the first and second electrodes 750, 760 may be located directly atop the upper and lower surfaces 783, 784 of the passageway 785. Specifically, because the first and second electrodes 750, 760 are located within the passageway 785, there may not be a need to recess the electrodes 750, 760 relative to the upper and lower surfaces 783, 784 of the passageway 785 because the passageway itself will prevent direct contact between the user's oral cavity surfaces and tongue with the first and second electrodes 750, 760.

In the exemplified embodiment, each of the first depressions 530 and each of the first electrodes 550 is axially spaced apart (in a direction of the axis G-G) along the upper surface 783 of the passageway 785. Similarly, each of the second depressions 540 and each of the second electrodes 560 is axially spaced apart (in a direct of the axis G-G) along the lower surface 784 of the passageway 785. Of course, depending on the specific orientation and arrangement of the depressions 530, 540 and the electrodes 550, 560, they may be transversely spaced apart (in a direction of the axis H-H) or obliquely spaced apart in other embodiments.

Although in the exemplified embodiment only the first electrodes 750 (which all have the same electrical charge) are located on the upper surface 783 of the passageway 785 and only the second electrodes 760 (which all have the same electrical charge) are located on the lower surface 784 of the passageway 785, this is not required in all embodiments. Specifically, in other embodiments one or more of the first electrodes 750 and one or more of the second electrodes 760 may be positioned on the upper surface 783. Similarly, one or more of the first electrodes 750 and one or more of the second electrodes 760 may be positioned on the lower surface 784. Other variations will be described below with reference to FIGS. 19B and 19C.

Furthermore, in the exemplified embodiment an exposed surface 751 of the first electrodes 750 is recessed relative to the upper surface 783 of the passageway 785 and an exposed surface 761 of the second electrodes 760 is recessed relative to the lower surface 784 of the passageway 785. However, the invention is not to be so limited and the exposed surfaces 751, 761 of the first and second electrodes 750, 760 may be flush with the upper and lower surfaces 783, 784 of the passageway 785 or they may protrude beyond the upper and lower surfaces 783, 784 of the passageway 785 in various alternative embodiments. Regardless of whether the first and/or second electrodes 750, 760 are recessed relative to, flush with, or protrude from the respective upper and lower surfaces 783, 784 of the passageway 785, the exposed surfaces 751, 761 of the first and second electrodes 750, 760 face the passageway 785. Furthermore, in the exemplified embodiment the exposed surfaces 751, 761 of the first and second electrodes 750, 760 face one another within the passageway 785.

Despite facing each other within the passageway 785, in the exemplified embodiment the first electrodes 750 on the upper surface 783 of the passageway 785 are axially offset from the second electrodes 760 on the lower surface 784 of the passageway 785. Thus, a reference plane that is perpendicular to the front surface and/or rear surface 711, 712 of the head 710 that intersects one of the first electrodes 750 will not also intersect one of the second electrodes 760, and vice versa. Thus, the first electrodes 750 are aligned with a portion of the lower surface 784 of the passageway 785 rather than being aligned with the second electrodes 760 and the second electrodes 760 are aligned with a portion of the upper surface 783 of the passageway 785 rather than being aligned with the first electrodes 750. This helps to prevent ions that are released from the first and/or second electrodes 750, 760 (when they are sacrificial electrodes) from passing onto the other one of the first and/or second electrodes 750, 760. Specifically, when the ions are released they have a tendency to attract to the oppositely charged electrodes. By axially offsetting the first and second electrodes 750, 760, the ions that are released are more likely to flow within the saliva or toothpaste slurry into the user's oral cavity to provide the user with a benefit than to be attached into the oppositely charged electrode. The same purpose may be achieved with the use of a barrier, which may be in the form of a plate-like member suspended within the passageway 785 between the upper and lower surfaces 783, 784 thereof.

Figure 19A:
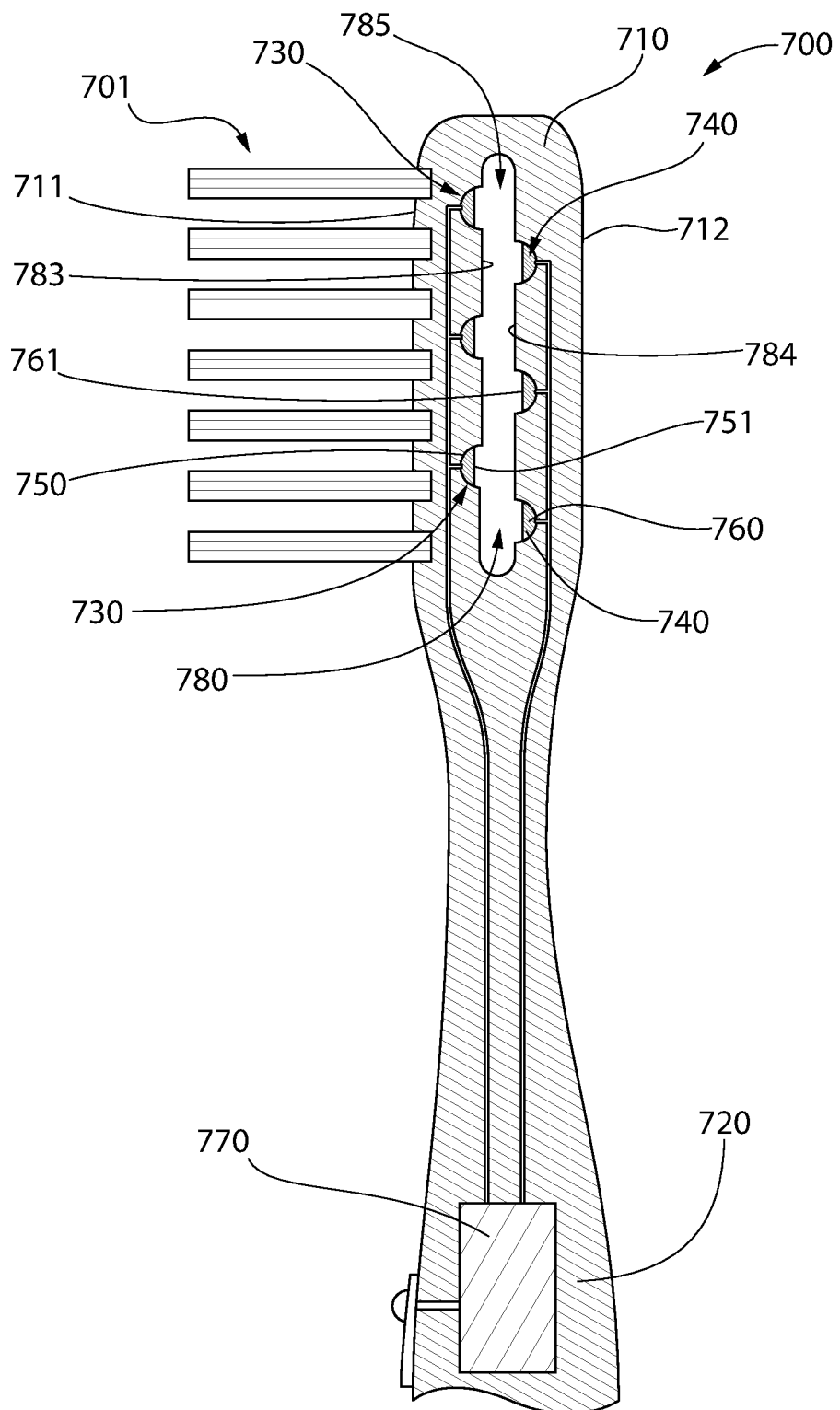
FIG. 19A is a cross-sectional view taken along line IXA-IXA of FIG. 17.
Figure 19B:
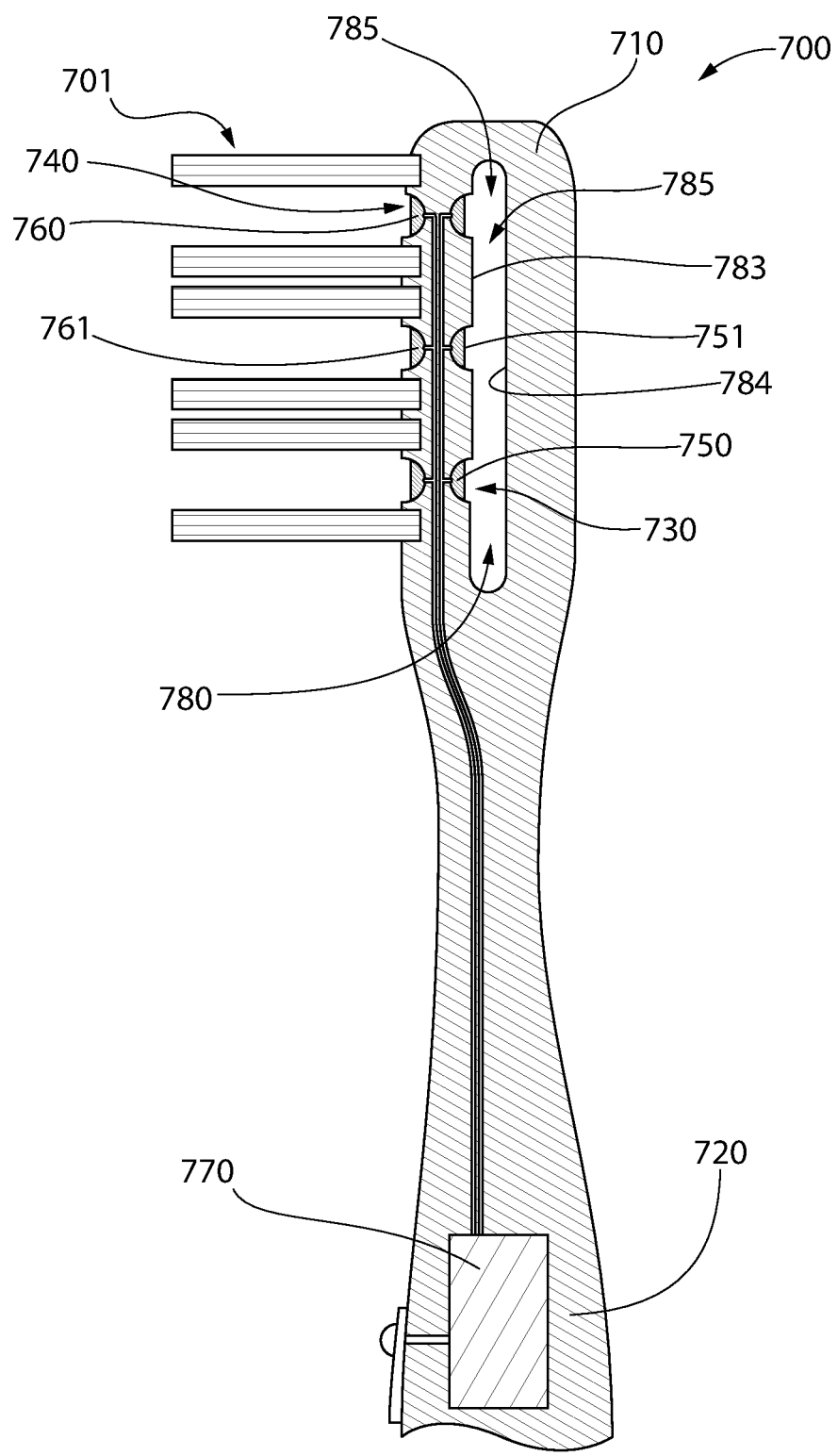
FIG. 19B is a cross-sectional view taken along line IXA-IXA of FIG. 17 in accordance with a first alternative embodiment.

Referring now to FIG. 19B, an alternative embodiment of the oral care implement 700 is illustrated. In this embodiment, the plurality of first depressions 730 having the first electrodes 750 therein are formed into the upper surface 783 of the passageway 785 formed by the through-hole similar to the embodiment of FIG. 19B. However, in this embodiment instead of the second depressions 740 with the second electrodes 760 therein being located on the lower surface 784 of the passageway 785, they are formed on the front surface 711 of the head 710. Specifically, in this embodiment the plurality of second depressions 740 are formed into the front surface 711 of the head 710. The plurality of second electrodes 760 are positioned within the second depressions 740 so that the second electrodes 760 are located on the front surface 711 of the head 710. As with the previously described embodiments, the exposed surfaces 751 of the first electrodes 750 may be recessed relative to the upper surface 783 of the passageway 785 and the exposed surfaces 761 of the second electrodes 760 may be recessed relative to the front surface 711 of the head 710.

Of course, in other embodiments there may be depressions with first electrodes 750 therein on the lower surface 784 of the passageway 785 and depression with second electrodes 760 therein on the rear surface 712 of the head 710. In still other embodiments the depressions with the first electrodes 750 may be located on the upper surface 784 of the passageway 785 and the depressions with the second electrodes 760 may be located on the rear surface 712 of the head 710. In further embodiments, the depression with the first electrodes 750 may be located on the front surface 711 of the head 710 and the depressions with the second electrodes 760 may be located on the lower surface 784 of the passageway 785. Thus, variations in the positioning of the first and second electrodes 750, 760 are possible. In such embodiments, portions of the head 710 (i.e., the portion between the front surface 711 and the passageway 785 and the portion between the rear surface 712 and the passageway 785) may form a barrier to prevent ions from passing from one of the electrodes to the other as discussed above.

Figure 19C:
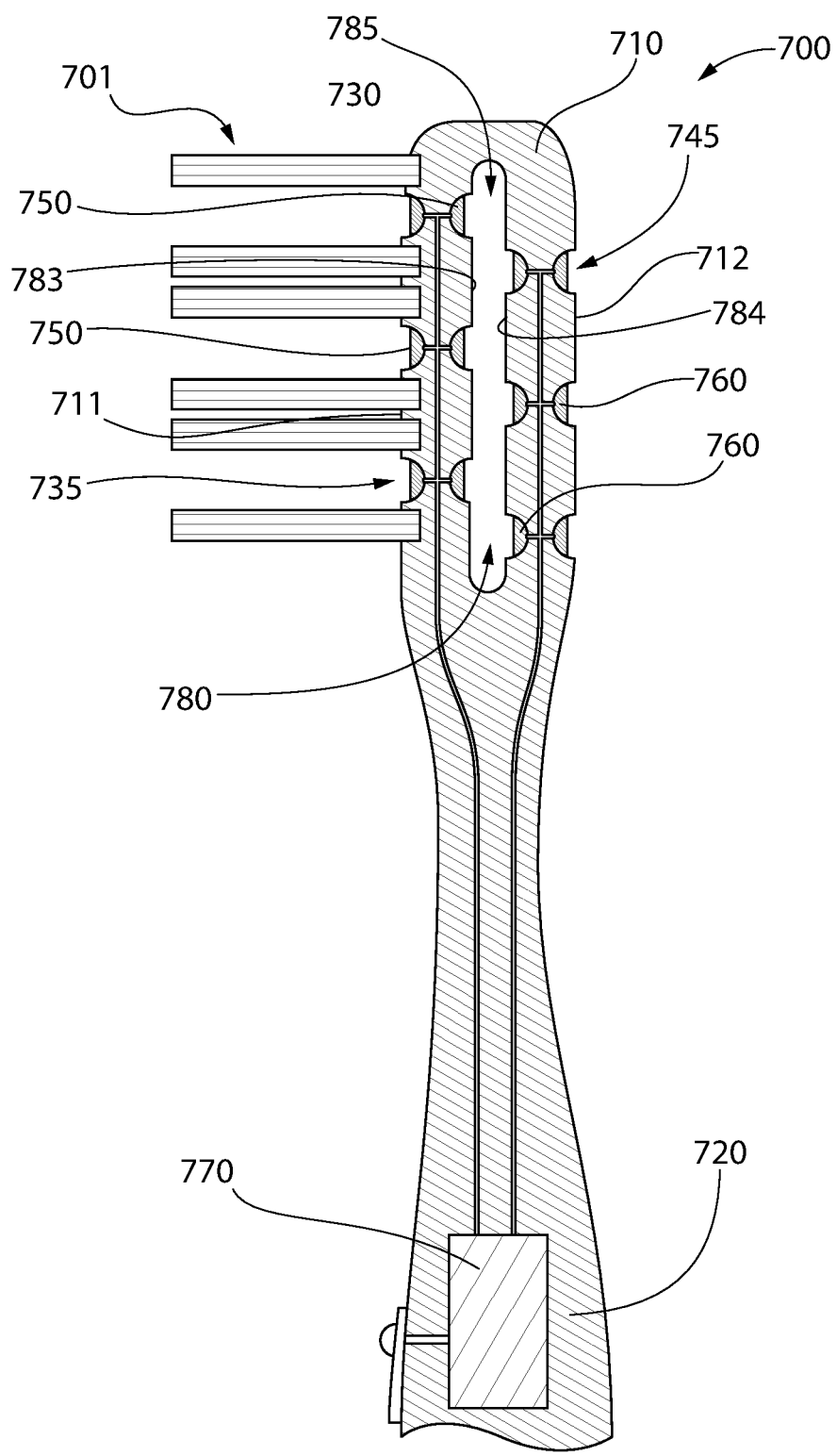
FIG. 19C is a cross-sectional view taken along line IXA-IXA of FIG. 17 in accordance with a second alternative embodiment.

Referring to FIG. 19C, yet another embodiment of the oral care implement 700 is illustrated. In this embodiment, there are a plurality of depressions 730 on the upper surface 783 of the passageway 785, a plurality of depressions 735 on the front surface 711 of the head 710, a plurality of depressions 740 on the lower surface 784 of the passageway 785, and a plurality of depression 745 on the rear surface 712 of the head 710. In this embodiment, one or more of the first electrodes 750 is positioned within each of the depressions 730 on the upper surface 783 of the passageway 785 and each of the depression 735 on the front surface 711 of the head 710. Furthermore, one or more of the second electrodes 760 is positioned within each of the depressions 740 on the lower surface 783 of the passageway 785 and each of the depressions 745 on the rear surface 712 of the head 710. In this embodiment, similarly charged electrodes 750 are positioned on the front surface 711 of the head 710 and on the upper surface 783 of the passageway 785 and similarly charged electrodes 760 are positioned on the rear surface 712 of the head 710 and on the lower surface 784 of the passageway 785.

However, this could be modified in any manner. For example, the first electrodes 750 could be on the front surface 711 of the head 710 and the rear surface 712 of the head 710 with the second electrodes 760 positioned on the upper and lower surfaces 783, 784 of the passageway 785. Alternatively, the first electrodes 750 could be on the front surface 711 of the head 710 and the lower surface 784 of the passageway 785 while the second electrodes 760 are on the upper surface 783 of the passageway 785 and the rear surface 712 of the head 710. In still other embodiments, at least one of the first electrodes 750 and at least one of the second electrodes 760 may be positioned on at least one of the front and rear surfaces 711, 712 of the head 710 and/or at least one of the upper and lower surfaces 783, 784 of the passageway 785. In some embodiments, at least one of the first electrodes 750 and at least one of the second electrodes 760 may be positioned on each of the front and rear surfaces 711, 712 of the head 710 and the upper and lower surfaces 783, 784 of the passageway 785. Thus, modifications to the particular locations for the first and second electrodes 750, 760 are possible within the scope of the invention described herein so long as the functionality described herein is achieved.

Figure 20:
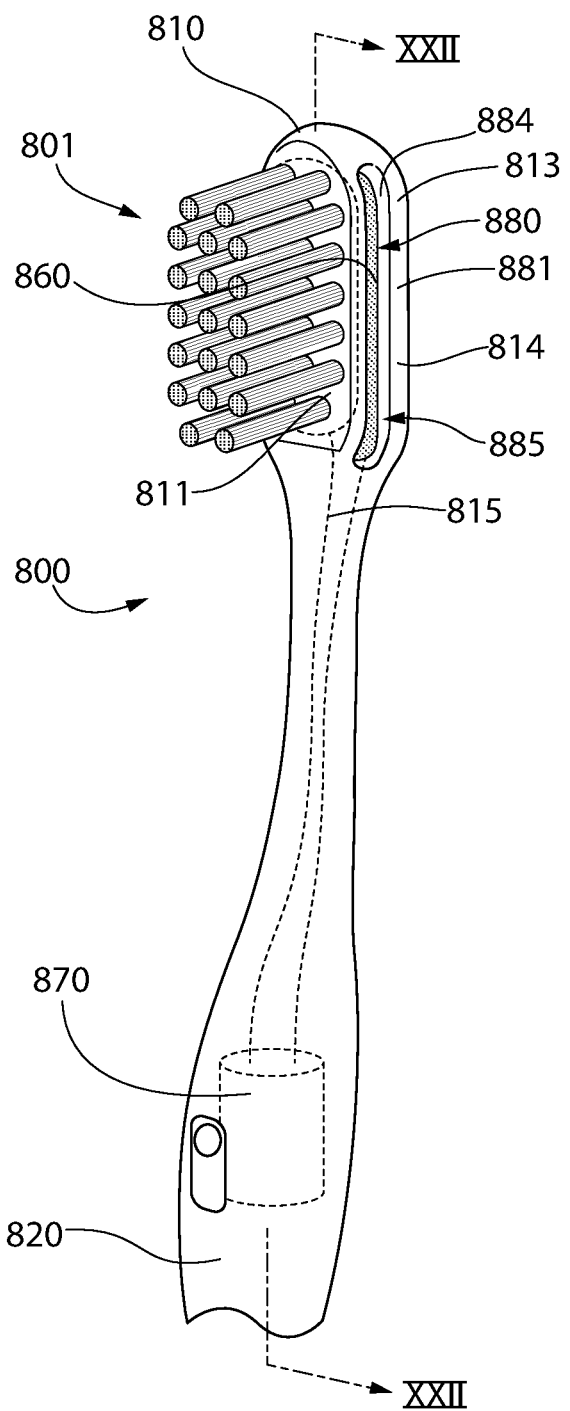
FIG. 20 is a front perspective view of an oral care implement in accordance with a seventh embodiment of the present invention.
Figure 21:
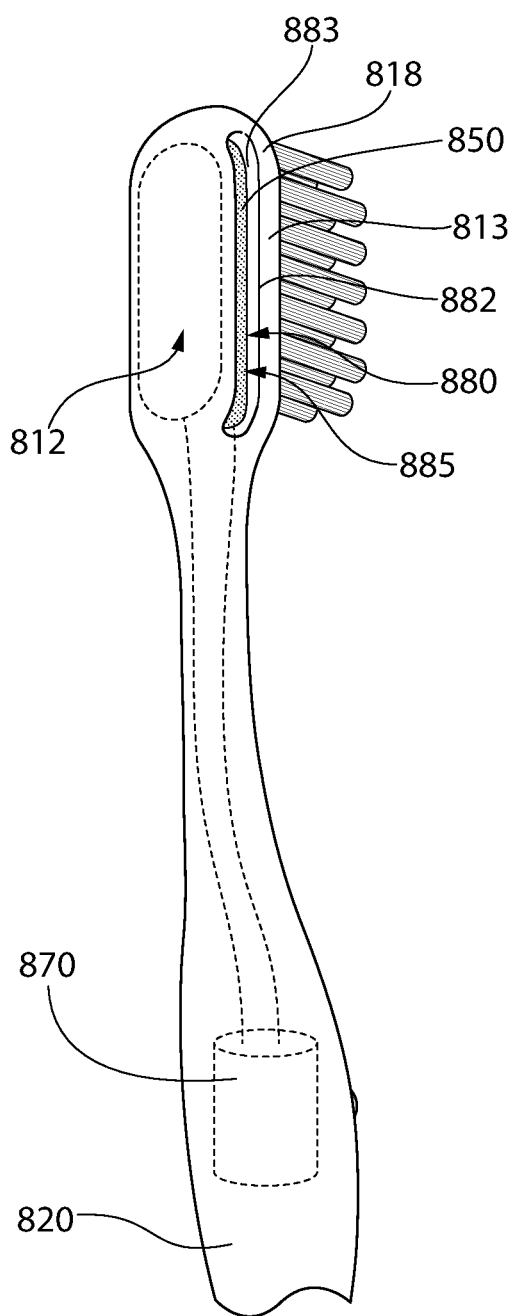
FIG. 21 is a rear perspective view of the oral care implement of FIG. 20.
Figure 22:
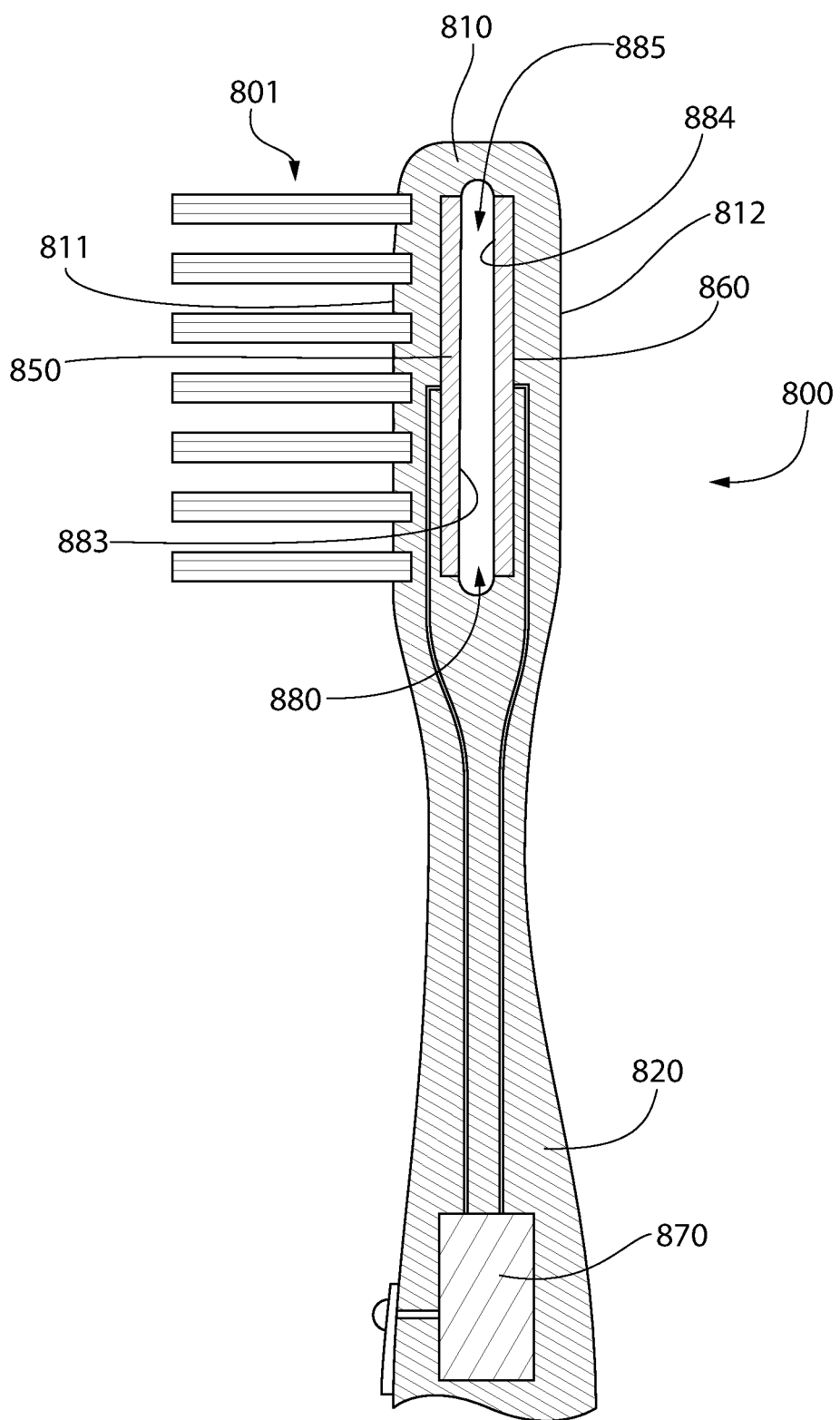
FIG. 22 is a cross-sectional view taken along line XXII-XXII of FIG. 20.

Referring to FIGS. 20-22 concurrently, an oral care implement 800 will be described in accordance with an embodiment of the present invention. Certain features of the oral care implement 800 are illustrated in the drawings but not described herein, it being understood that the description of the similar feature of the oral care implements 100, 700 provided above is applicable. The oral care implement 800 generally comprises a head 810, a handle 820, and a neck 815 extending between the handle 820 and the head 810. The head 810 has an exposed outer surface that comprises a front surface 811, an opposite rear surface 812, and a side surface 813 extending between the front and rear surfaces 811, 812. A plurality of tooth cleaning elements 801 are coupled to the head 810 to extend from the front surface 811 of the head 800. Although not illustrated, a soft tissue cleaner may be coupled to the rear surface 812 of the head 810 as described above.

The structure of the head 810 is generally identical to the structure of the head 710 of the oral care implement 700 described above. Thus, the head 810 comprises a through-hole 880 extending from a first lateral portion 814 of the side surface 813 to a second lateral portion 818 of the side surface 813. The through-hole 880 extends from a first opening 881 in the first lateral portion 814 of the side surface 813 of the head 810 to a second opening 882 in the second lateral portion 818 of the side surface 813 of the head 810. The through-hole 880 forms a transverse passageway 885 through the head 810 that is defined by an upper surface 883 and a lower surface 884.

The main difference between the oral care implement 800 and the oral care implement 700 is in the structure/type of the electrodes. Specifically, in this embodiment a first electrode 850 is provided on the upper surface 883 of the passageway 885 and a second electrode 860 is provided on the lower surface 884 of the passageway 885. Each of the first and second electrodes 850, 860 is operably coupled to a power source 870, which may be located in the handle 820 as shown or in other locations as described herein. The first and second electrodes 850, 860 are coupled to the power source 870 so as to have opposite electrical charges. Thus, the first electrode 850 may have a positive electrical charge and the second electrode 860 may have a negative electrical charge, or vice versa. In this embodiment, each of the first and second electrodes 850, 860 are mesh electrodes. The mesh-style electrodes may form a grid-like structure with two sets of parallel strips that intersect each other (e.g., similar to the structure of a door and window screen). Forming the first and second electrodes 850, 860 as mesh electrodes gives them a greater surface area to ensure simultaneous contact with saliva during use of the oral care implement 800 for generation of an electric field and release of ions. In that regard, at least one, and possibly both, of the first and second electrodes 850, 860 may be sacrificial electrodes as discussed herein above.

In the exemplified embodiment, the first electrode 850 forms most of if not the entirety of the upper surface 883 of the passageway 885 while the second electrode 860 forms most of if not the entirety of the lower surface 884 of the passageway 885. Although in the exemplified embodiment the mesh electrodes are positioned on the opposing upper and lower surfaces 883, 884 of the passageway, the invention is not to be so limited in all embodiments. In some embodiments, the first and second mesh electrodes 850, 860 may both be positioned on the same one of the upper and lower surfaces 883, 884 of the passageway 885 in an axially spaced apart manner. In other embodiments, the first and second mesh electrodes 850, 860 may both be positioned on the front or rear surfaces 811, 812 of the head 810 (such embodiment may omit the through-hole 880 and passageway 885). In other embodiments the first and second mesh electrodes 850, 860 may be positioned on any combination of the front and rear surfaces 811, 812 of the head 810 and the upper and lower surfaces 883, 884 of the passageway 880. Thus, variation in the particular location of the mesh-style electrodes on the oral care implement is possible and falls within the scope of the invention described herein.

Figure 23:
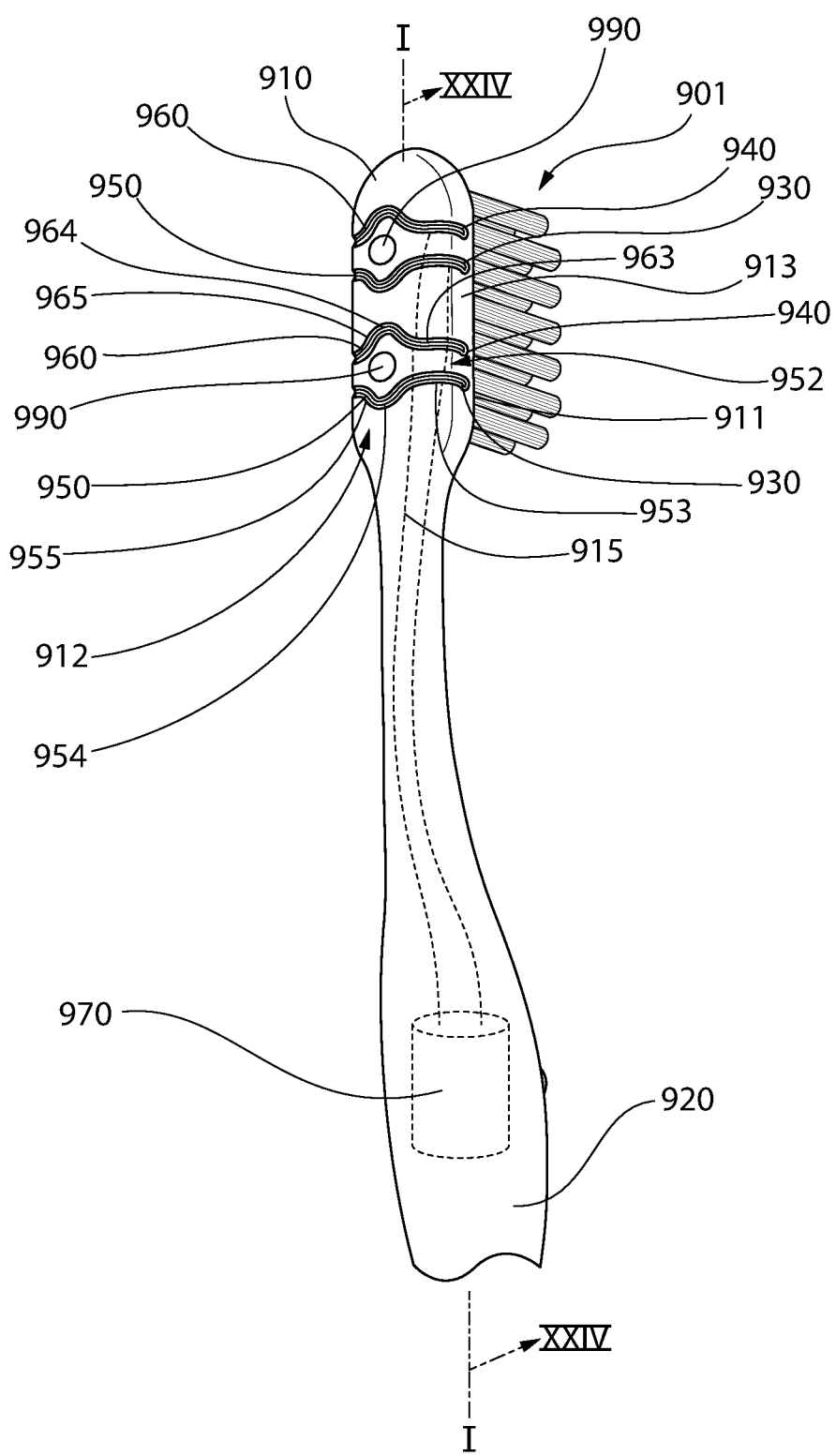
FIG. 23 is a rear perspective view of an oral care implement in accordance with an eighth embodiment of the present invention.
Figure 24:
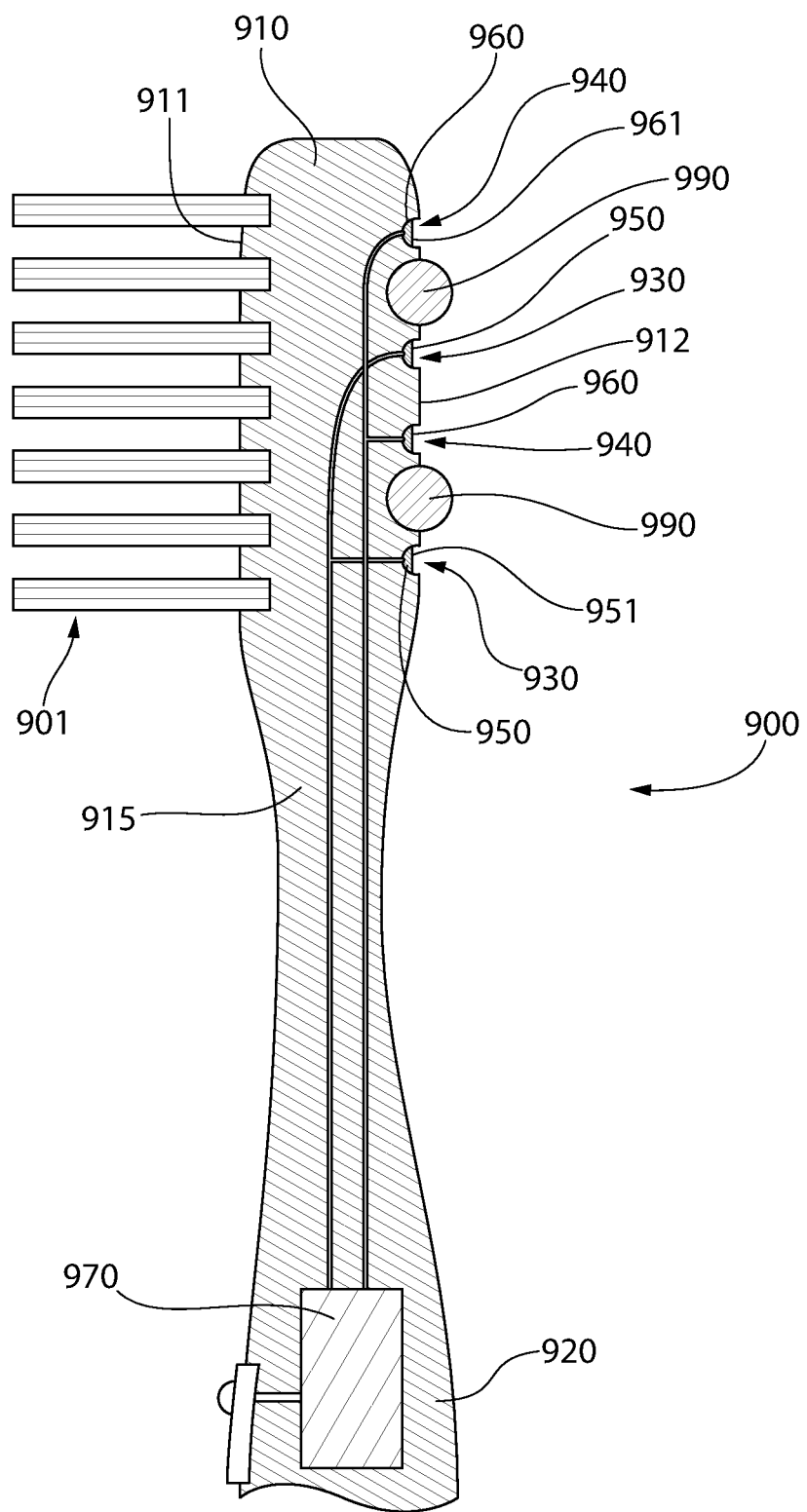
FIG. 24 is a cross-sectional view taken along line XXIV-XXIV of FIG. 23.

Referring now to FIGS. 23 and 24, an oral care implement 900 will be described in accordance with another embodiment of the present invention. Certain features of the oral care implement 900 are illustrated in the drawings but not described herein, it being understood that the description of the similar feature of the oral care implements 100, 300-800 provided above is applicable. The oral care implement 900 generally comprises a head 910, a handle 920, and a neck 915 extending between the handle 920 and the head 910. The oral care implement 900 and specifically the head 910 extends along a longitudinal axis I-I. The head 910 has an exposed outer surface that comprises a front surface 911, an opposite rear surface 912, and a side surface 913 extending between the front and rear surfaces 911, 912. A plurality of tooth cleaning elements 901 are coupled to the head 910 to extend from the front surface 911 of the head 900. Although not illustrated, a soft tissue cleaner may be coupled to the rear surface 912 of the head 910 as described above.

In this embodiment, the oral care implement 900 comprises a plurality of first depressions 930 having a first electrode 950 therein and a plurality of second depression 940 having a second electrode therein 960. Each of the first and second electrodes 950, 960 is operably coupled to a power source 970 so that the first and second electrodes 950, 960 have opposite electrical charges. In the exemplified embodiment, the first and second electrodes 950, 960 are disposed within the first and second depressions 930, 940 so that they have exposed surfaces 951, 961 that are recessed relative to the outer surface of the head 910. However, the invention is not to be so limited in all embodiments of the oral care implement 900. Each of the first and second electrodes 950, 960 are elongated in a direction generally transverse to the longitudinal axis I-I of the head 910. In the exemplified embodiment, each of the first electrodes 950 and each of the second electrodes 960 are located on the rear surface 912 of the head 910. However, the invention is not to be so limited and one or more of the first and/or second electrodes 950, 960 may be located on the front surface 911 of the head 910 in other embodiments. At least one, and possibly both, of the first and second electrodes 950, 960 may be a sacrificial electrode in some embodiments, the details of which have been described above.

In this embodiment, the oral care implement 900 further comprises an oral care agent dispenser 990. In the exemplified embodiment the oral care agent dispenser 990 is a solid release polymer comprising an oral care agent. Thus, during use of the oral care implement 900 the oral care agent dispenser 990 will get wet with saliva and toothpaste slurry and will begin to dissolve, thereby releasing the oral care agent into the user's oral cavity. In such an embodiment, the oral care agent dispenser 990 may dissolved slowly over time during multiple uses of the oral care implement 900 or it may entirely dissolved within a single use. In other embodiments, the oral care agent dispenser 990 may be a capsule that ruptures during use of the oral care implement 900 to dispense its contents into the user's oral cavity. Regardless of the manner in which it operates, the oral care agent dispenser 990 contains an oral care agent and releases it into a user's mouth during toothbrushing.

In certain embodiments the oral care agent may be a mouthwash, a dentifrice, a tooth whitening agent such as peroxide containing tooth whitening compositions, or the like. Other oral care agents include, for example without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. In certain embodiments the oral care agent is free of (i.e., is not) toothpaste. Instead, the oral care agent in such embodiments may be intended to provide benefits in addition to merely brushing one's teeth. Other suitable oral care materials could include lip balm or other materials that are typically available in a semi-solid state. Furthermore, in still other embodiments the oral care agent can be a natural ingredient, such as for example without limitation, lotus seed; lotus flower, bamboo salt; jasmine; corn mint; camellia; aloe; gingko; tea tree oil; xylitol; sea salt; vitamin C; ginger; cactus; baking soda; pine tree salt; green tea; white pearl; black pearl; charcoal powder; nephrite or jade and Ag/Au+. Thus, the invention is not intended to be limited by the specific type of oral care agent used in some embodiments.

In the exemplified embodiment, there are two of the oral care agent dispensers 990 and they are both located on the rear surface 912 of the head 910. Specifically, each of the oral care agent dispensers 990 is located on and protrudes from the rear surface 912 of the head 910. In other embodiments, a single oral care agent dispenser 990 may be used. In still other embodiments, multiple oral care agent dispensers 990 may be used and located on the front surface 911 of the head 910 only, or on both of the front and rear surfaces 911, 912 of the head 910. When multiple oral care agent dispensers 990 are used, they may comprise the same oral care agent or different oral care agents. In the exemplified embodiment, the first and second oral care agent dispensers 990 are located on the longitudinal axis I-I in a spaced apart manner. However, the oral care agent dispensers 990 may be positioned at other locations on the rear surface 912 of the head 910 so as to be offset from the longitudinal axis I-I.

In the exemplified embodiment, the oral care agent dispensers 990 are illustrated as protruding from the exposed outer surface of the head 910. However, the invention is not to be so limited in all embodiments and the oral care agent dispensers 990 may be recessed relative to the exposed outer surface of the head 910 in other embodiments. Furthermore, the oral care agent dispensers 990 may be located within the through-hole 980 of the oral care implement 700 described previously. Thus, the oral care agent dispensers 990 need not be placed for direct contact with the user's oral surfaces. Rather, the oral care agent dispensers 990 merely need to be positioned in such a way that saliva and/or toothpaste slurry can contact the oral care agent dispensers 990 to cause the oral care agent dispensers 990 to release the oral care agent into the saliva and/or toothpaste slurry so that it may enter into the user's mouth to provide a particular oral care benefit.

In the exemplified embodiment, the first and second electrodes 950, 960 are arranged in pairs such that each pair of electrodes (containing one of the first electrodes 950 and one of the second electrodes 960) surrounds one of the oral care agent dispensers 990. Thus, for each of the oral care agent dispensers 990, the first electrode 950 is located on a first side of the oral care agent dispenser 990 and the second electrode 960 is located on a second side of the oral care agent dispenser 990. Stated another way, the oral care agent dispenser 990 may be located on a transverse reference plane that intersects the front and rear surfaces 911, 912 of the head 910 and is oriented transverse to the longitudinal axis I-I. The first electrode 950 is located on a first side of the transverse reference plane and the second electrode 960 is located on a second side of the transverse reference plane.

The first and second electrodes 950, 960 of each pair of electrodes are axially spaced apart from one another so that a transverse pathway 952 is defined between the first and second electrodes 950, 960. The oral care agent dispenser 990 is located within the transverse pathway 952.

In the exemplified embodiment the first electrode 950 comprises a first linear section 953 located adjacent a first lateral portion of the side surface 913 of the head 910, a curved section 954, and a second linear section 955 located adjacent a second lateral portion of the side surface 913 of the head 910. The first and second lateral portions of the side surface 913 of the head 910 are located on opposite sides of the longitudinal axis I-I. The curved section 954 of the first electrode 950 is located between the first and second linear sections 953, 955. Furthermore, in the exemplified embodiment the curved section 954 of the first electrode 950 is located adjacent to (and in axial alignment with) the oral care agent dispenser 990.

Similarly, the second electrode 960 comprises a first linear section 963 located adjacent the first lateral portion of the side surface 913 of the head 910, a curved section 964, and a second linear section 965 located adjacent the second lateral portion of the side surface 913 of the head 910. The curved section 964 of the second electrode 960 is located between the first and second linear sections 963, 965. Furthermore, in the exemplified embodiment the curved section 964 of the second electrode 960 is located adjacent to (and in axial alignment with) the oral care agent dispenser 990. Moreover, the curved section 964 of the second electrode 960 is axially aligned with the curved section 954 of the first electrode 950. In the exemplified embodiment, the curved sections 954, 964 of the first and second electrodes 950, 960 have concave sides facing the oral care agent dispenser 990. However, the invention is not to be so limited in all embodiments and a convex side of one or both of the curved sections 954, 964 of the first and second electrodes 950, 960 may face the oral care agent dispenser 990 in other embodiments.

In the exemplified embodiment the curved sections 954, 964 of the first and second electrodes 950, 960 collectively surround the oral care agent dispenser 990. Having linear and curved sections ensures that the first and second electrodes 950, 960 are positioned sufficiently close to the oral care agent dispenser 990 to ensure that ions released from the first and/or second electrodes 950, 960 will interact with the oral care agent released from the oral care agent dispenser 990. In some embodiments, the electrodes 950, 960 may include only the curved sections 954, 964 and the linear sections 953, 955, 963, 965 may be omitted.

Although in the exemplified embodiment there are two oral care agent dispensers 990, each with one of the first and second electrodes 950 adjacent thereto, the invention is not to be so limited in all embodiments. In one alternative embodiment, the oral care implement 900 may include a first electrode 950 and a second electrode 960 each of which is oriented so as to be elongated in a direction parallel to the longitudinal axis I-I. In such an embodiment, the first and second electrodes 950, 960 may each include two curved sections such that one of the curve sections is adjacent to each of the oral care agent dispensers 990. These types of permutations and modifications should be readily understood and appreciated by persons skilled in the art.

Figure 25:
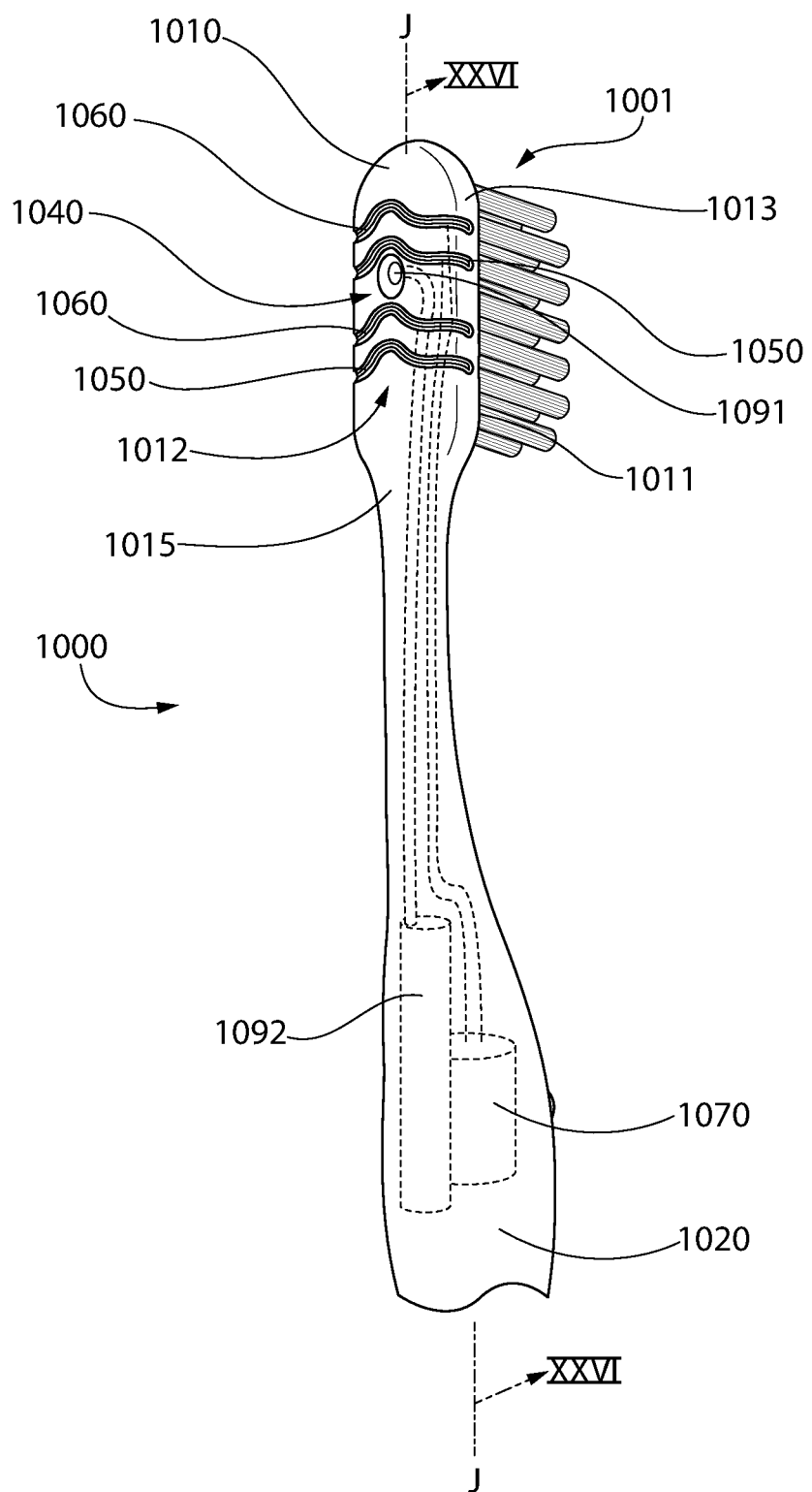
FIG. 25 is a rear perspective view of an oral care implement in accordance with an ninth embodiment of the present invention.
Figure 26:
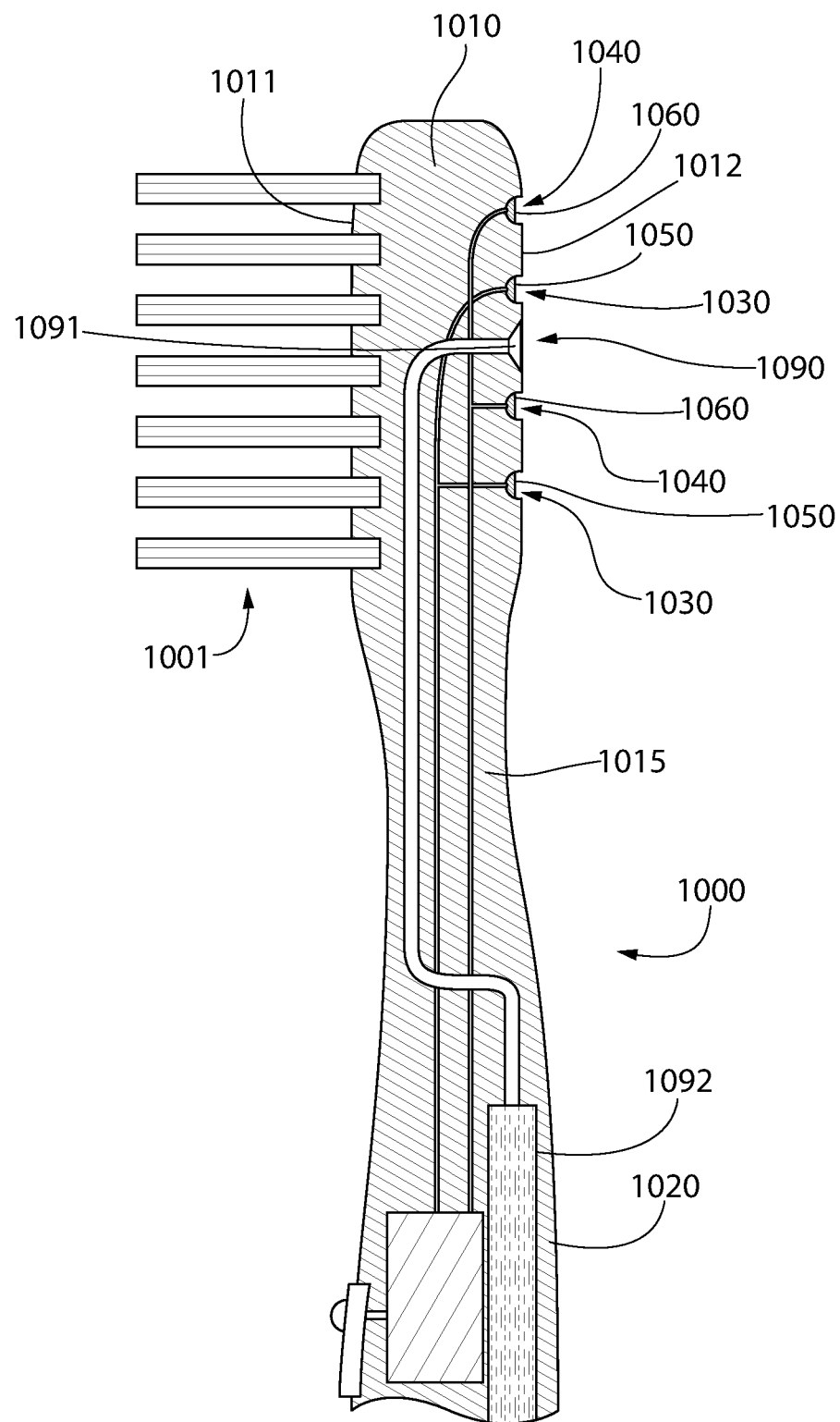
FIG. 26 is a cross-sectional view taken along line XXVI-XXVI of FIG. 25.

Referring to FIGS. 25-26, another embodiment of an oral care implement 1000 will be described. Certain features of the oral care implement 1000 are illustrated in the drawings but not described herein, it being understood that the description of the similar feature of the oral care implements 100, 300-900 provided above is applicable. The oral care implement 100 generally comprises a head 1010, a handle 1020, and a neck 1015 extending between the handle 1020 and the head 1010. The oral care implement 1000 and specifically the head 1010 extends along a longitudinal axis J-J. The head 1010 has an exposed outer surface that comprises a front surface 1011, an opposite rear surface 1012, and a side surface 1013 extending between the front and rear surfaces 1011, 1012. A plurality of tooth cleaning elements 1001 are coupled to the head 1010 to extend from the front surface 1011 of the head 1010. Although not illustrated, a soft tissue cleaner may be coupled to the rear surface 1012 of the head 1010 as described above.

The oral care implement 1000 comprises first and second electrodes 1050, 1060 that are disposed within first and second depressions 1030, 1040, respectively, as has been described in detail throughout this disclosure. The first and second electrodes 1050, 1060 are each operably coupled to a power source 1070 to have an opposite electrical charge. Specifically, the first electrodes 1050 have a first electrical charge (positive or negative) and the second electrodes 1060 have a second electrical charge (positive or negative) that is opposite the first electrical charge of the first electrodes 1050. The oral care implement 1000 also comprises an oral care agent dispenser 1090. The oral care implement 1000 of FIGS. 25-26 is very similar to the oral care implement 900 of FIGS. 23-24 except with regard to the arrangement of the first and second electrodes 1050, 1060 and the details of the oral care agent dispenser 1090.

In this embodiment, the oral care implement 1000 comprises a reservoir 1092 located within the handle 1020. Of course, the reservoir 1092 could be located within the neck 1015 or even the head 1010 in other embodiments. The reservoir 1092 stores an oral care agent, which may be any of the oral care agents noted herein above during the description of the oral care implement 900. In this embodiment, the oral care agent dispenser 1090 comprises an outlet 1091 located on the rear surface 1012 of the head 1011. The outlet 1091 is fluidly coupled to the reservoir 1092 so that the oral care agent stored within the reservoir 1092 can be dispensed into a user's oral cavity via the outlet 1091. In certain embodiments the oral care implement 1000 may include one or more pumps to dispense the oral care agent from the reservoir 1092 to the outlet 1091. In other embodiments, the oral care agent may flow from the reservoir 1092 to the outlet 1091 via capillary action through a capillary tube.

In the exemplified embodiment, the outlet 1091 is located on the rear surface 1012 of the head 1010. However, the invention is not to be so limited in all embodiments and the outlet 1091 may be located on the front surface 1011 of the head 1010 (within the field of the tooth cleaning elements 1001) in other embodiments. Similarly, although the first and second electrodes 1050, 1060 are located on the rear surface 1012 of the head 1010 in the exemplified embodiment, they may be located on the front surface 1011 of the head 1010 or on both of the front and rear surfaces 1011, 1012 of the head 1010 in other embodiments.

In the exemplified embodiment, there are two pairs of first and second electrodes 1050, 1060 on the rear surface of the head 1010. The first pair of electrodes 1050, 1060 is located on a first side of the outlet 1091 and the second pair of electrodes 1050, 1060 is located on a second side of the outlet 1091 that is opposite the first side of the outlet 1091. However, the invention is not to be so limited and in other embodiments the first and second electrodes 1050, 1060 of each pair of electrodes may be located on opposite sides of the outlet 1091. Specifically, one of the first electrodes 1050 may be located adjacent the outlet 1091 and between the outlet 1091 and the distal end of the head 1010 and one of the second electrodes 1060 may be located adjacent to the outlet 1091 and between the outlet 1091 and the handle 1020. Thus, some variation is possible within the scope of the present invention.

Figure 27:
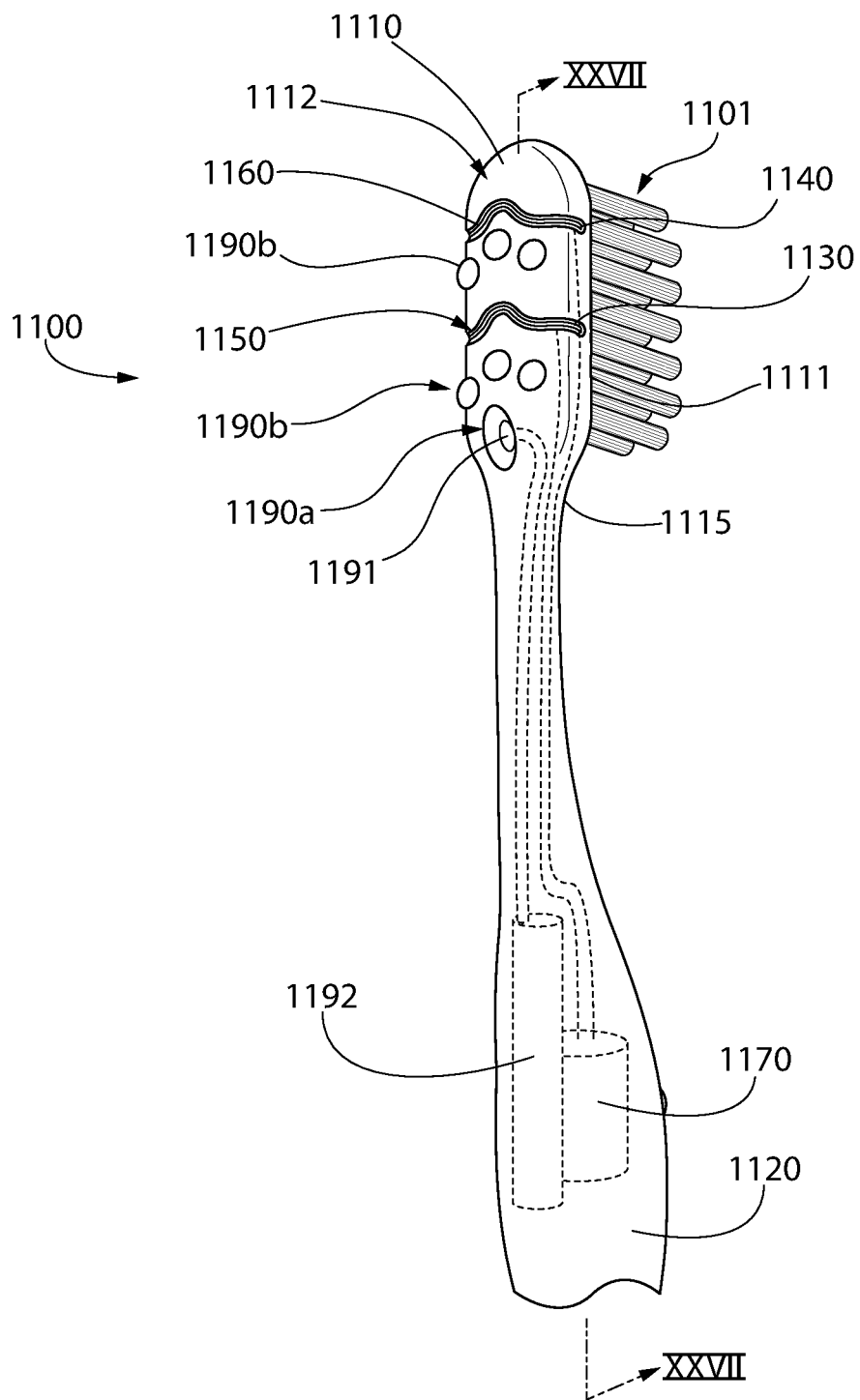
FIG. 27 is a rear perspective view of an oral care implement in accordance with an tenth embodiment of the present invention.
Figure 28:
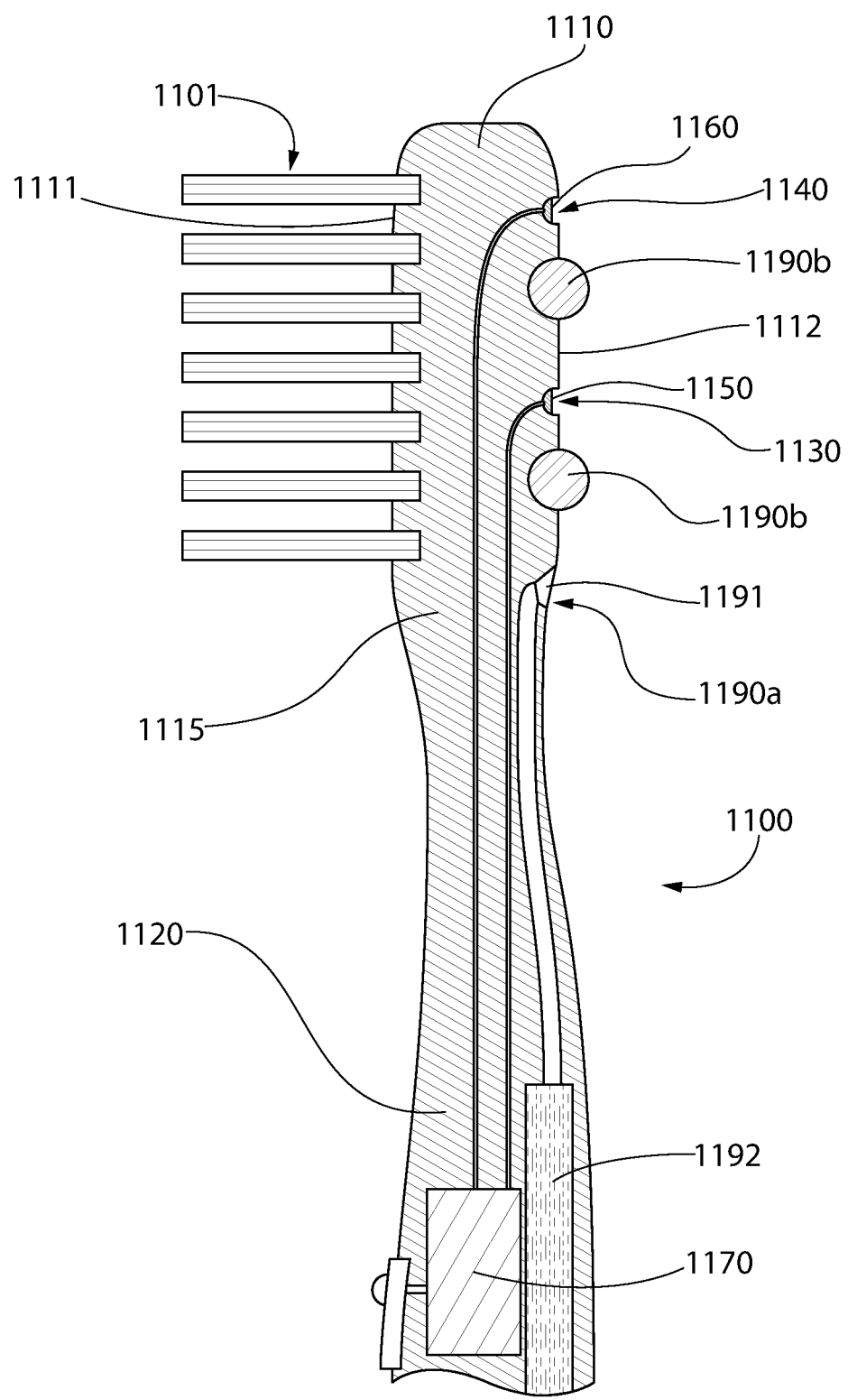
FIG. 28 is a cross-sectional view taken along line XXVIII-XXVIII of FIG. 27.

Referring to FIGS. 27 and 28 concurrently, an oral care implement 1100 is illustrated in accordance with a final embodiment of the present invention. The oral care implement is a combination of the oral care implement 900 and the oral care implement 1000. Certain detail so that the oral care implement 1100 will not be described herein, it being understood that the descriptions of the oral care implements 100 and 300-1000, and particularly the oral care implements 900, 1000, is applicable. Thus, for features shown in FIGS. 27-28 and not described, reference to the previous disclosure is applicable.

The oral care implement 1100 generally comprises a head 1110, a handle 1120, and a neck 1115 extending between the head 1110 and the handle 1120. The head 1110 has a front surface 1111 with tooth cleaning elements 1101 extending therefrom and an opposite rear surface 1112. In the exemplified embodiment, first and second electrodes 1150, 1160 are located on the rear surface 1112 of the head 1110 within depressions 1130, 1140 formed into the rear surface 1112 of the head 1110. Of course, the electrodes 1150, 1160 may be positioned at other locations on the head 1110 in other embodiments as has been described thoroughly herein. The electrodes 1150, 1160 are each operably coupled to a power source 1170 so that the first electrodes 1150, have an opposite charge relative to the second electrodes 1160. The electrodes 1150, 1160 may be recessed relative to the exposed outer surface (i.e., front surface 1111, rear surface 1112, or side surface that extends therebetween) as has been described above. Furthermore, at least one of the first and second electrodes 1150, 1160, and possibly both, may be a sacrificial electrode in some embodiments.

In this embodiment the oral care implement 1100 comprises a reservoir 1192 for storing an oral care agent. Furthermore, the oral care implement 1100 comprises a first oral care agent dispenser 1190*b* comprising a solid release polymer (as described above with reference to FIGS. 23 and 24) and a second oral care agent dispenser 1190*a* comprising an outlet 1191 that is fluidly coupled to the oral care agent in the reservoir 1192. The oral care agent in the reservoir 1192 and the solid release polymers may be the same oral care agent or different oral care agents, depending on the desired result. In the exemplified embodiment there are six solid release polymers illustrated, however in other embodiments there may simply be a single solid release polymer or any desired number of solid release polymers. Each of the solid release polymers may comprise the same oral care agent or different oral care agents. Thus, in this embodiment there is both dispensing of oral care material from solid release polymers and from an outlet that is coupled to a reservoir located within the oral care implement 1100.

In the exemplified embodiment, one of the first electrodes 1150 and one of the second electrodes 1160 are illustrated. Of course, more than one of each of the first and second electrodes 1150, 1160 may be included on the oral care implement 1100 in other embodiments. In this embodiment the first and second electrodes 1150, 1160 are located adjacent to and on opposite sides of a set of three of the solid release polymers. However, the first and second electrodes 1150, 1160 may be positioned adjacent to the outlet 1191 instead of or in addition to being adjacent to the solid release polymers. Regardless of the specific location and structure of the electrodes 1150, 1160, it may be desirable in some embodiments to have the electrodes 1150, 1160 sufficiently close to the outlet 1191 and/or the solid release polymers so that ions released from the electrodes 1150, 1160 can mix with the oral care agent to enhance the effect and performance of the oral care agent and/or to produce a unique active agent that is not possible with just the oral care agents or just the electrodes 1150, 1160.

Some embodiments described above describe oral care implements incorporating a sacrificial electrode to release ions that provide benefits in the oral cavity. To the extent that some implementations contemplate placing electrical components and/or generating electrical fields in the oral cavity, it should be noted that the devices may be operated with sufficiently low current and voltage that will not have an adverse effect to the oral cavity or the user. For example, currents on the order of not more than 5 milliamps and voltages of no greater than about 3 Volts may be used to generate ions according to some embodiments of this disclosure. Furthermore, in some embodiments the electrodes are recessed within the oral care implement body so that exposed surfaces of the electrodes will not come into direct contact with the user's oral cavity surfaces, which will also reduce any adverse effects such as electric shock or the like.

Each of the electrodes described herein can take on any number of different forms, including being wire-type electrodes, mesh-type electrodes, or any other physical configuration and/or combination including wound coils, flat electrodes, porous electrodes, and the like. The number of electrodes, windings, and the surface area of the electrodes are not limiting of the present invention in all embodiments and these may vary. The electrodes can be made from any material and can have both semiconducting and conducting properties to target a desired effect. In some embodiments the electrodes may be plated with a sacrificial metal material that makes the electrodes sacrificial electrodes as described herein and in other embodiments the electrodes may be formed entirely from a sacrificial metal. In various embodiments, the electrodes can interact with saliva, toothpaste, liquid chemistry, solid release polymers, and/or any combinations to enhance the effect and performance of the chemistry delivery.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
   a handle;
   a head coupled to the handle, the head having a front surface and a rear surface opposite the front surface;
   a plurality of tooth cleaning elements extending from the front surface of the head;
   a soft tissue cleaner on the rear surface of the head, the soft tissue cleaner formed of an elastomeric material and comprising a protuberance field; and
   a first electrode and a second electrode each operably coupled to a power source, the first and second electrodes spaced apart from one another and substantially surrounding the protuberance field.

2. The oral care implement according to claim 1 wherein the first and second electrodes are located at least partially on the rear surface of the head.

3. The oral care implement according to claim 1 wherein the head further comprises a side surface extending between the front and rear surfaces, and wherein each of the first and second electrodes is at least partially located on the side surface of the head.

4. The oral care implement according to claim 1 wherein the head extends from a proximal end to a distal end along a longitudinal axis, and wherein the first electrode is located on a first side of the longitudinal axis and the second electrode is located on a second side of the longitudinal axis.

5. The oral care implement according to claim 4 wherein the first and second electrodes are spaced apart by a first gap located on the longitudinal axis at the proximal end of the head and a second gap located on the longitudinal axis at the distal end of the head.

6. The oral care implement according to claim 1 wherein the soft tissue cleaner comprises a pad portion located on the rear surface of the head and a plurality of protuberances extending from the pad portion and forming the protuberance field.

7. The oral care implement according to claim 1 wherein the soft tissue cleaner is spaced apart from each of the first and second electrodes.

8. The oral care implement according to claim 7 wherein the head comprises an outer surface that comprises the front surface, the rear surface, and a side surface extending between the front and rear surfaces, and wherein a portion of the outer surface of the head separates each of the first and second electrodes from the soft tissue cleaner.

9. The oral care implement according to claim 1 wherein the protuberance field extends from a first end to a second end along a longitudinal axis of the head, and wherein the first and second electrodes extend axially beyond the first and second ends of the protuberance field.

10. The oral care implement according to claim 1 wherein the plurality of tooth cleaning elements comprise bristles.

11. The oral care implement according to claim 1 wherein each of the first and second electrodes is disposed within a depression in the head so that an exposed surface of the first and second electrodes are recessed relative to an exposed outer surface of the head.

12. The oral care implement according to claim 1 wherein one of the first and second electrodes is an anode and the other of the first and second electrodes is a cathode.

13. An oral care implement comprising:
a handle;
a head coupled to the handle, the head having a front surface and a rear surface opposite the front surface;
a plurality of tooth cleaning elements extending from the front surface of the head;
a soft tissue cleaner formed of an elastomeric material positioned on the rear surface of the head, the soft tissue cleaner comprising a protuberance field and a pad portion located on the rear surface of the head;
a first electrode and a second electrode each operably coupled to a power source, located at least partially within the protuberance field of the soft tissue cleaner, and at a least partially embedded in the pad portion; and
wherein at least one of the first and second electrodes is a sacrificial electrode.

14. The oral care implement according to claim 13 wherein the soft tissue cleaner comprises a plurality of protuberances extending from an upper surface of the pad portion and forming the protuberance field.

15. The oral care implement according to claim 14 wherein an exposed outer surface of the first and second electrodes is flush with the upper surface of the pad portion of the soft tissue cleaner.

16. The oral care implement according to 14 wherein an exposed outer surface of the first and second electrodes is recessed relative to the upper surface of the pad portion of the soft tissue cleaner.

17. The oral care implement according to claim 14 wherein an exposed outer surface of each of the first and second electrodes is recessed relative to distal tips of the plurality of protuberances.

18. An oral care implement comprising:
a handle;
a head coupled to the handle, the head having a front surface and a rear surface opposite the front surface;
a plurality of tooth cleaning elements extending from the front surface of the head;
a soft tissue cleaner formed of an elastomeric material positioned on the rear surface of the head, the soft tissue cleaner comprising a pad portion; and
a first electrode and a second electrode each operably coupled to a power source, at least one of the first and second electrodes embedded within the pad portion of the soft tissue cleaner.

19. The oral care implement according to claim 18 wherein at least one of the first and second electrodes is a sacrificial electrode.

* * * * *